(12) United States Patent
Tsujikawa

(10) Patent No.: US 11,589,787 B2
(45) Date of Patent: Feb. 28, 2023

(54) DROWSINESS ESTIMATING DEVICE, DROWSINESS ESTIMATING METHOD, AND DROWSINESS ESTIMATING PROGRAM RECORDING MEDIUM

(71) Applicant: NEC CORPORATION, Tokyo (JP)

(72) Inventor: Masanori Tsujikawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 252 days.

(21) Appl. No.: 16/956,081

(22) PCT Filed: Dec. 20, 2017

(86) PCT No.: PCT/JP2017/045725
§ 371 (c)(1),
(2) Date: Jun. 19, 2020

(87) PCT Pub. No.: WO2019/123569
PCT Pub. Date: Jun. 27, 2019

(65) Prior Publication Data
US 2020/0390379 A1  Dec. 17, 2020

(51) Int. Cl.
*A61B 13/00* (2006.01)
*A61B 5/16* (2006.01)
(Continued)

(52) U.S. Cl.
CPC .............. *A61B 5/163* (2017.08); *A61B 3/113* (2013.01); *A61B 5/1103* (2013.01); *A61B 5/18* (2013.01)

(58) Field of Classification Search
CPC ....... A61B 5/163; A61B 3/113; A61B 5/1103; A61B 5/18
(Continued)

(56) References Cited

U.S. PATENT DOCUMENTS

2011/0216181 A1* 9/2011 Yoda ................. A61B 5/18
348/78
2011/0313259 A1* 12/2011 Hatakeyama ......... B60W 40/08
600/300
(Continued)

FOREIGN PATENT DOCUMENTS

JP  11-339200 A   12/1999
JP  11339200 A  * 12/1999
(Continued)

OTHER PUBLICATIONS

Hiroki Kitajima et al., "Prediction of Automobile Driver Sleepiness (1st Report, Rating of Sleepiness Based on Facial Expression and Examination of Effective Predictor Indexes of Sleepiness)", Transactions of the Japan Society of Mechanical Engineers (Edition C), Sep. 1997, pp. 3059-3066, vol. 63, No. 613.
(Continued)

*Primary Examiner* — Naomi J Small
(74) *Attorney, Agent, or Firm* — Sughrue Mion, PLLC

(57) ABSTRACT

This drowsiness estimating device estimates a subject's drowsiness from a time-series signal of the subject's eye-openness width. A filtering circuitry filters the time-series signal of the eye-openness width to eliminate signal changes due to the subject blanking and outputs the filtered time-series signal of eye-openness. A feature calculator calculates a feature from at least the filtered time-series signal of the eye-openness width. A drowsiness estimator estimates a drowsiness evaluated value from the feature and outputs an estimated result. The feature calculator includes at least a first feature calculation circuit that calculates a variation of the filtered time-series signal of the eye-openness width within a feature calculation window width and outputs the variation as a first feature.

20 Claims, 33 Drawing Sheets

(51) Int. Cl.
*A61B 3/113* (2006.01)
*A61B 5/11* (2006.01)
*A61B 5/18* (2006.01)

(58) Field of Classification Search
USPC .......................................................... 600/558
See application file for complete search history.

(56) References Cited

U.S. PATENT DOCUMENTS

| | | | | |
|---|---|---|---|---|
| 2014/0205149 | A1* | 7/2014 | Nakamura | A61B 5/163 382/103 |
| 2016/0367127 | A1* | 12/2016 | Wulf | A61B 3/0025 |
| 2017/0080947 | A1 | 3/2017 | Boos | |

FOREIGN PATENT DOCUMENTS

| | | | |
|---|---|---|---|
| JP | 2006-109980 A | | 4/2006 |
| JP | 2008-099884 A | | 5/2008 |
| JP | 2008-201285 A | | 9/2008 |
| JP | 2008210285 A | * | 9/2008 |
| JP | 2009-146377 A | | 7/2009 |
| JP | 2009146377 A | * | 7/2009 |
| JP | 2017-006675 A | | 1/2017 |
| JP | 2017-079055 A | | 4/2017 |
| WO | 2010/092860 A1 | | 8/2010 |

OTHER PUBLICATIONS

"Research on Vehicle-Based Driver State/Performance Monitoring; Development, Validation, and Refinement of Algorithms for Detection of Driver Drowsiness", U.S. Department of Transportation, National Highway Traffic Safety Administration, Dec. 1994, Chapter Two, pp. 24-43.

Takayuki Mineyama et al., "Estimating reaction time by analyzing eyelid image", ITS, Sep. 26, 2006, pp. 69-72.

International Search Repot for PCT/JP2017/045725 dated Mar. 20, 2018 (PCT/ISA/210).

Written Opinion of the International Searching Authority for PCT/JP2017/045725 dated Mar. 20, 2018 (PCT/ISA/237).

* cited by examiner

DROWSINESS ESTIMATING DEVICE, DROWSINESS ESTIMATING METHOD, AND DROWSINESS ESTIMATING PROGRAM RECORDING MEDIUM

CROSS REFERENCE TO RELATED APPLICATIONS

This application is a National Stage of International Application No. PCT/JP2017/045725 filed Dec. 20, 2017.

TECHNICAL FIELD

This invention relates to a drowsiness estimating device, a drowsiness estimating method, and a drowsiness estimating program recording medium.

BACKGROUND ART

In the middle of growing labor shortage due to a decrease in working-age population resulting from a declining birthrate and an aging population, it has been tried to replace those jobs, which have been carried out by human beings until now, with robots or A (artificial intelligence). Under the circumstances, it is essential for human beings to maintain and improve productivity of intellectual labor which is difficult for the robots or the AI.

However, a person cannot exert his/her intellectual ability due to influence of drowsiness (low wakefulness) or stress (high wakefulness) and then his/her intellectual productivity decreases. In order to carry out control of an intra-office environment in which the intellectual labor is performed so as to prevent lowering of the intellectual productivity due to a change in wakefulness, it is necessary to estimate an arousal level accompanied with the lowering of the intellectual productivity, namely, in which wakefulness the person is. This invention relates to a technique for estimating, among the arousal levels, a low arousal level or drowsiness.

It is known that the drowsiness is rated using drowsiness evaluated values of, for example, 1 to 5 (see Non-Patent Literature 1). According to Non-Patent Literature 1, among the drowsiness evaluated values, 1 represents "not drowsy at all", 2 represents "slightly drowsy", 3 represents "drowsy", 4 represents "very drowsy", and 5 represents "extremely drowsy".

For the purpose to detect drowsy driving, a large number of techniques for estimating the above-mentioned drowsiness from a condition of opening of an eye (that will be called an "eye-openness width" hereinafter) have been proposed. Here, the eye-openness width has a value normalized in a range between 0 and 1.

For instance, Patent Literature 1 discloses a condition estimating apparatus which estimates an awareness state of a driver of a car or the like. The condition estimating apparatus disclosed in Patent Literature 1 detects the eye-openness width of the driver, creates a frequency distribution of frequency of detection of the eye-openness width, extracts an extreme value of the frequency distribution, and estimates the state of the driver based on a temporal change of the extreme value of the frequency distribution.

In addition, Patent Literature 2 discloses a method for ascertaining a state of drowsiness of a driver of a motor vehicle. Movements of at least one eyelid of eyes of the driver are detected, and the state of drowsiness of the driver is determined as a function of the detected movements. Particularly, the drowsiness is estimated from periodicity (0.2 Hz to 1 Hz) of the movements of closing the eyes from the normal eye-openness width by a maximum of 40%, in particular, by a maximum of 30%.

Further, in Patent Literature 3, it was found that, when a person felt a little drowsy, a variation in eye-open time (the time for which the eyes are open between eye blinks) is decreased. Using this finding, the physiological condition is determined.

Furthermore, in Non-Patent Literature 2, a ratio (eye-closure ratio) of a time interval during which the eyes are closed, for example, 80% or more, is used as a drowsiness index to detect the drowsiness.

CITATION LIST

Patent Literature

PTL 1: JP 2008-099884 A
PTL 2: JP 2017-079055 A
PTL 3: WO2010/092860A1

Non Patent Literature

NPL 1: Hiroki KITAJIMA and three others, "Prediction of Automobile Driver Sleepiness (1st Report, Rating of Sleepiness Based on Facial Expression and Examination of Effective Predictor Indexes of Sleepiness", Transactions of the Japan Society of Mechanical Engineers (Edition C), (September 1997), Vol. 63, No. 613, p 3059-3066

NPL 2: "Research on Vehicle-Based Driver State/Performance Monitoring; Development, Validation, and Refinement of Algorithms For Detection of Driver Drowsiness", U.S. Department of Transportation, (December 1994), Chapter Two, p. 24-43

SUMMARY INVENTION

Technical Problem

However, the methods described in Patent Literatures 1 to 3 and Non-Patent Literature 2 mentioned above have a problem that the drowsiness cannot be estimated with sufficiently high accuracy depending on various conditions such as a time window width within which the drowsiness is estimated and a sampling rate of data of the eye-openness width.

It is an object of this invention to provide a drowsiness estimating device, a drowsiness estimating method, and a drowsiness estimating program recording medium, which are capable of resolving the above-mentioned problem.

Solution to Problem

A mode of the present invention is a drowsiness estimating device for estimating, from a time-series signal of an eye-openness width of a subject, drowsiness of the subject, the drowsiness estimating device comprising a filtering circuitry configured to filter the time-series signal of the eye-openness width so as to eliminate signal changes due to blinking of the subject therefrom to produce a filtered time-series signal of the eye-openness width; a feature calculator configured to calculate a feature from at least the filtered time-series signal of the eye-openness width; and a drowsiness estimator configured to estimate a drowsiness evaluated value from the feature to produce an estimated result, wherein the feature calculator at least includes a first feature calculation circuit configured to calculate a variation in the filtered time-series signal of the eye-openness width within a feature calculation window width ($T_M$) [sec] to produce the variation as a first feature.

A mode of the present invention is a drowsiness estimating method of estimating, from a time-series signal of an eye-openness width of a subject, drowsiness of the subject, the drowsiness estimating method comprising filtering, by a filtering circuitry, the time-series signal of the eye-openness width so as to eliminate signal changes due to blinking of the subject therefrom to produce a filtered time-series signal of the eye-openness width; calculating, by a feature calculator, a feature from at least the filtered time-series signal of the eye-openness width; and estimating, by a drowsiness estimator, a drowsiness evaluated value from the feature to produce an estimated result, wherein, in the feature calculator, a first feature calculation circuit calculates at least a variation in the filtered time-series signal of the eye-openness width within a feature calculation window width ($T_M$) [sec] to produce the variation as a first feature.

A mode of the present invention is a drowsiness estimating program recording medium having recorded thereon a drowsiness estimating program for causing a computer to execute processing for estimating, from a time-series signal of an eye-openness width of a subject, drowsiness of the subject, the drowsiness estimating program causing the computer to execute a filtering procedure of filtering the time-series signal of the eye-openness width so as to eliminate signal changes due to blinking of the subject therefrom to produce a filtered time-series signal of the eye-openness width; a feature calculation procedure of calculating a feature from at least the filtered time-series signal of the eye-openness width; and a drowsiness estimation procedure of estimating a drowsiness evaluated value from the feature to produce an estimated result, wherein the feature calculation procedure at least includes a first feature calculation procedure of calculating a variation in the filtered time-series signal of the eye-openness width within a feature calculation window width ($T_M$) [sec] to produce the variation as a first feature.

Advantageous Effect of Invention

According to the present invention, it is possible to estimate drowsiness with high accuracy independent of various conditions such as a time window width within which the drowsiness is estimated and a sampling rate of data of the eye-openness width.

DESCRIPTION OF EMBODIMENTS

Hereinafter, preferred example embodiments of the present invention will be described in detail with reference to the drawings.

First Example Embodiment

Figure 1:
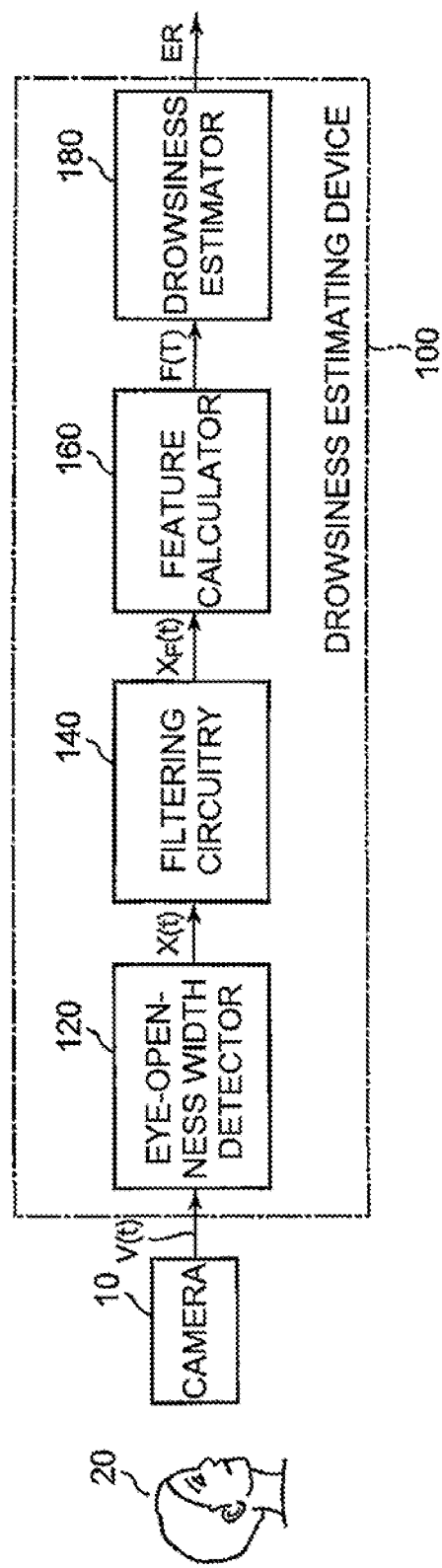
FIG. 1 is a block diagram for illustrating a configuration of a drowsiness estimating device according to a first example embodiment of this invention.

FIG. 1 is a block diagram for illustrating a configuration of a drowsiness estimating device 100 according to a first example embodiment of this invention. The illustrated drowsiness estimating device 100 may be implemented by a computer which operates under program control.

The illustrated drowsiness estimating device 100 is connected to a camera 10. The camera 10 takes a face image of a subject 20 to generate a moving image signal V(t) indicative of the taken face image. The generated moving image signal V(t) is supplied to the drowsiness estimating device 100. Herein, t is an index of time and is a frame number. In general, the moving image signal is a signal having a frame rate fs [frames/sec]. In the example being illustrated, fs is equal to 30. Accordingly, it is assumed in this example that the moving image signal V(t) is a signal having 30 [frames/sec].

Herein, the subject 20 may be, for example, a staff member who works in an office. In this case, the drowsiness estimating device 100 can be used as a device for estimating drowsiness of the staff member 20. Under such a circumstance, the camera 10 is mounted to a predetermined position of, for example, a monitor (display) of a personal computer or a display of a laptop computer, which is placed on a desk, to take the face image of the staff member (worker) 20 in question. The drowsiness estimating device 100 may be built into a computer body of the personal computer or the laptop computer or may be provided separately therefrom. In addition, the drowsiness estimating device 100 may be configured to be supplied with the moving image signal which is stored in a storage device built into the computer body or a storage device on a network.

On the other hand, the subject 20 may be a driver who drives (operates) a vehicle such as a motor vehicle, an electric train, a ship, or an airplane. In this case, the drowsiness estimating device 100 can be used as a device for estimating drowsiness of the driver 20. Under such a situation, the camera 20 is disposed at a dashboard of the motor vehicle, that is located in front of the driver 20, to take a face image of the driver 20 in question. The drowsiness estimating device 100 may be connected to an alarm which is not shown. In this event, when the drowsiness estimating device 10 estimates that the driver 20 is in a drowsy state, it may deliver a control signal for causing the alarm to generate an alert.

The drowsiness estimating device 100 comprises an eye-openness width detector 120, a filtering circuitry 140, a feature calculator 160, and a drowsiness estimator 180. The eye-openness width detector 120 detects an eye-openness width from the moving image signal. The filtering circuitry 140 filters a time-series signal of the eye-openness width. The feature calculator 160 calculates a feature from the filtered time-series signal. The drowsiness estimator 180 estimates drowsiness from the feature to produce an estimated result. Thereinafter, the respective parts will be described in detail.

The eye-openness width detector 120 image-processes the moving image signal V(t) to detect an eye-openness width of the subject 20 and produces a time-series signal X(t) of the eye-openness width of the subject 20.

Figure 2:
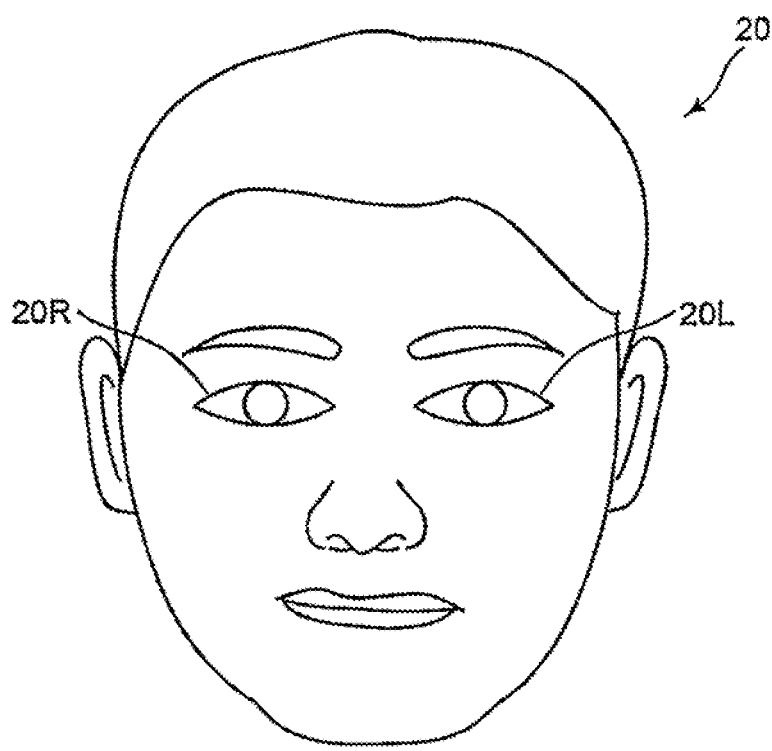
FIG. 2 is a schematic front view for illustrating an example of a subject to be photographed by a camera connected to the drowsiness estimating device illustrated in FIG. 1.

As shown in FIG. 2, the object 20 has a left eye 20L and a right eye 20R. Accordingly, the eye-openness width detector 120 may detect an eye-openness width of the left eye 20L and an eye-openness width of the right eye 20R to produce a time-series signal $X_L(t)$ of the eye-openness width of the left eye 20L and a time-series signal $X_R(t)$ of the eye-openness width of the right eye 20R, respectively. In this event, the above-mentioned time-series signal X(t) of the eye-openness width of the subject 20 may be obtained by signal-averaging the time-series signal $X_L(t)$ of the eye-openness width of the left eye 20L and the time-series signal $X_R(t)$ of the eye-openness width of the right eye 20R.

Figure 3:
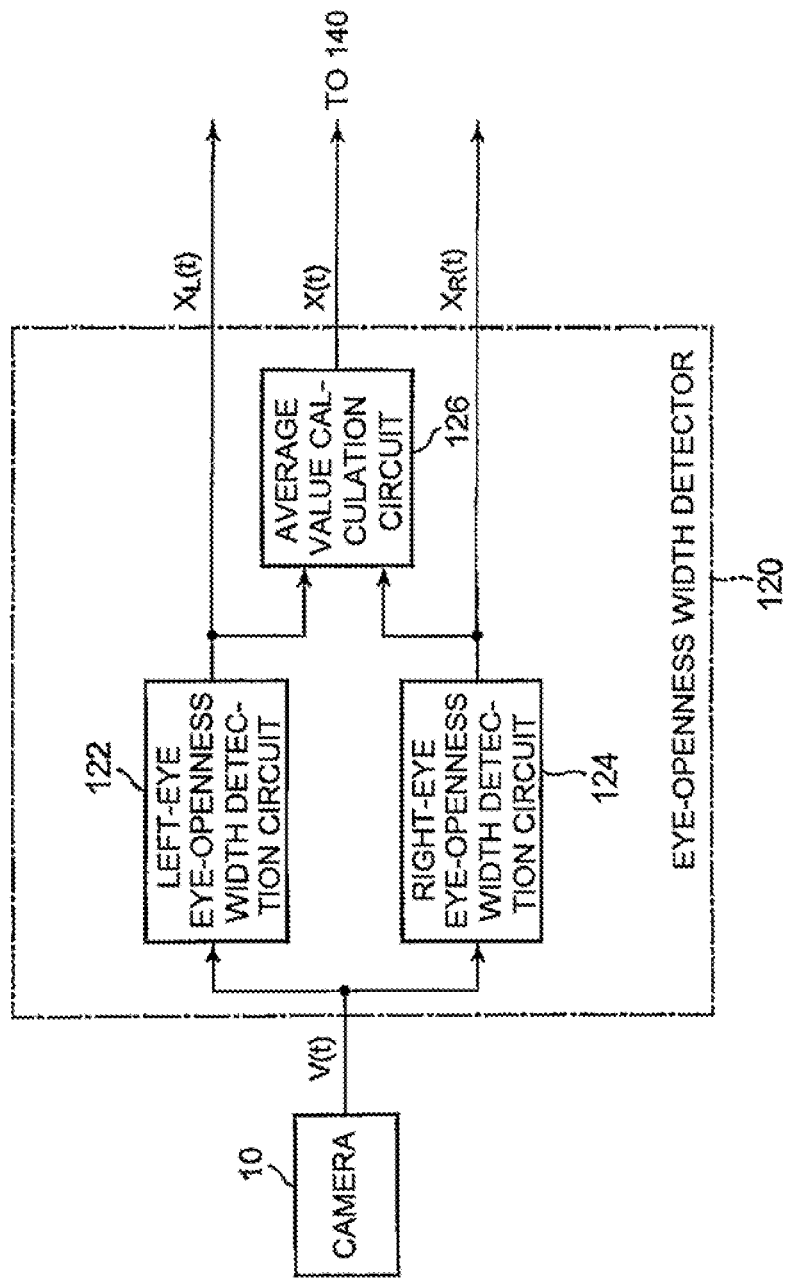
FIG. 3 is a block diagram for illustrating an example of an eye-openness width detector for use in the drowsiness estimating device illustrated in FIG. 1.

FIG. 3 is a block diagram for illustrating an example of the eye-openness width detector 120. The eye-openness width detector 120 comprises a left-eye eye-openness width detection circuit 122, a right-eye eye-openness width detection circuit 124, and an average value calculation circuit 126.

The left-eye eye-openness width detection circuit 122 extracts a region of the left eye 20L of the subject 20 from the moving image signal V(t), detects the eye-openness width of the left eye 20L, and produces the time-series signal $X_L(t)$ of the eye-openness width of the left eye 20L. Likewise, the right-eye eye-openness width detection circuit 124 extracts a region of the right eye 20R of the subject 20 from the moving image signal V(t), detects the eye-openness width of the right eye 20R, and produces the time-series signal $X_R(t)$ of the eye-openness width of the right eye 20R. It is noted that, for the left-eye eye-openness width detection circuit 122 and the right-eye eye-openness width detection circuit 124, the same circuit may be used. For instance, the time-series signal $X_R(t)$ of the eye-openness width of the right eye may be calculated by supplying the left-eye eye-openness width detection circuit 122 with the moving image signal of the right eye with right and left being reversed.

The average value calculation circuit 126 signal-averages the time-series signal $X_L(t)$ of the eye-openness width of the left eye 20L and the time-series signal $X_R(t)$ of the eye-openness width of the right eye 20R to calculate an averaged value, and produces the averaged value as the time-series signal X(t) of the eye-openness width of the subject 20. Accordingly, the time-series signal X(t) of the eye-openness width of the subject 20 is represented by the following Math. 1:

$$X(t)=\{X_L(t)+X_R(t)\}/2 \quad \text{[Math. 1]}$$

In this example, as each of the time-series signal $X_L(t)$ of the eye-openness width of the left eye 20L, the time-series signal $X_R(t)$ of the eye-openness width of the right eye 20R, and the time-series signal X(t) of the eye-openness width of the subject 20, a normalized value in a range between 0 and 1 is used.

Figure 4:
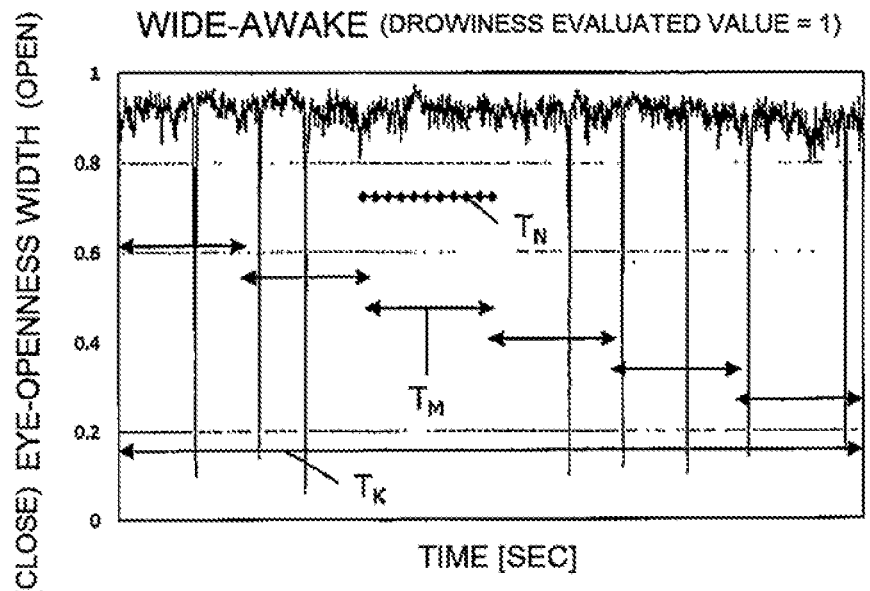
FIG. 4 is a waveform chart for illustrating an example of a time-series signal X(t) of an eye-openness width of the subject illustrated in FIG. 2 when the subject is wide-awake (drowsiness evaluated value=1).

FIG. 4 is a waveform chart for illustrating an example of the time-series signal X(t) of the eye-openness width of the subject 20, when the subject 20 is wide-awake (drowsiness evaluated value=1). On the other hand, FIG. 5 is a waveform chart for illustrating an example of the time-series signal X(t) of the eye-openness width of the subject 20, when the subject 20 is drowsy (drowsiness evaluated value≥3).

Figure 5:
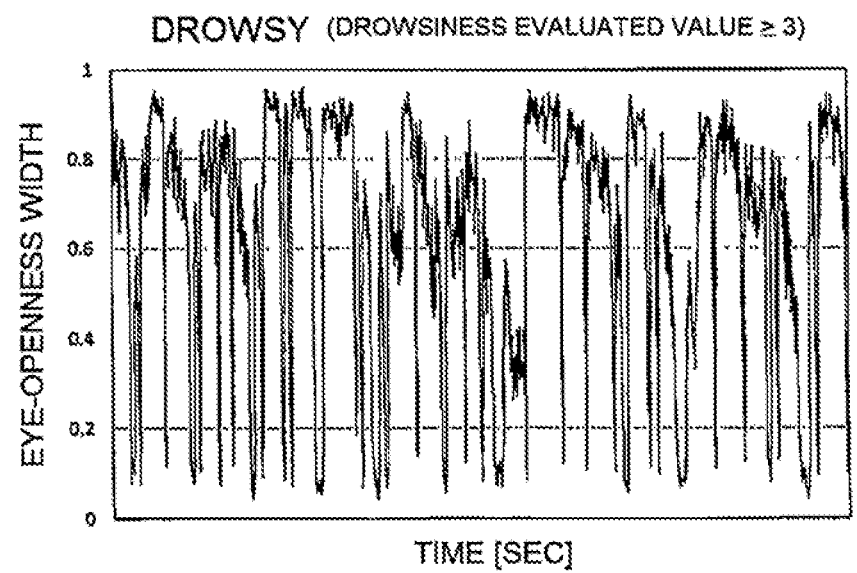
FIG. 5 is a waveform chart for illustrating an example of the time-series signal X(t) of the eye-openness width of the subject illustrated in FIG. 2 when the subject is drowsy (drowsiness evaluated value ≥3).

In each of FIGS. 4 and 5, the axis of abscissa represents a time [sec] whereas the axis of ordinate represents the eye-openness width. An eye-openness width of "0" indicates that the eyes of the subject 20 are perfectly closed whereas an eye-openness width of "1" indicates that the eyes of the subject 20 are perfectly opened.

Next, description will proceed to the filtering circuitry 140 of FIG. 1. The filtering circuitry 140 filters the time-series signal X(t) of the eye-openness width so as to eliminate, therefrom, signal changes due to blinking of the subject 20 and produces the filtered time-series signal $X_F(t)$ of the eye-openness width. The filtered time-series signal $X_F(t)$ of the eye-openness width is generally represented by the following Math. 2:

$$X_F(t)=F[X(t), \ldots, X(t-N+1)], \quad \text{[Math.2]}$$

where N represents the number of frames for filtering processing. Accordingly, the filtering circuitry 140 carries out the filtering processing per filtering calculation window width $T_N$ [sec]. Between the number N of frames and the filtering calculation window width $T_N$ [sec], there is a relationship which is represented by the following Math. 3:

$$N=T_N \times fs \quad \text{[Math. 3]}$$

For instance, as shown in FIG. 4, when the number N of frames is equal to three and the frame rate fs is equal to 30 [frames/sec], the filtering calculation window width $T_N$ [sec] becomes 0.1 [sec].

In this example, the filtering circuitry 140 substitutes the time-series signal X(t) of the eye-openness width with a predetermined value by filtering it per filtering calculation window width $T_N$ [sec] to produce a substituted signal as the filtered time-series signal $X_F(t)$ of the eye-openness width.

Although the filtering circuitry 140 of this example uses only the time-series signal X(t) of the eye-openness width, the time-series signal $X_L(t)$ of the eye-openness width of the left eye 20L and the time-series signal $X_R(t)$ of the eye-openness width of the right eye 20R may further be used.

Figure 6:
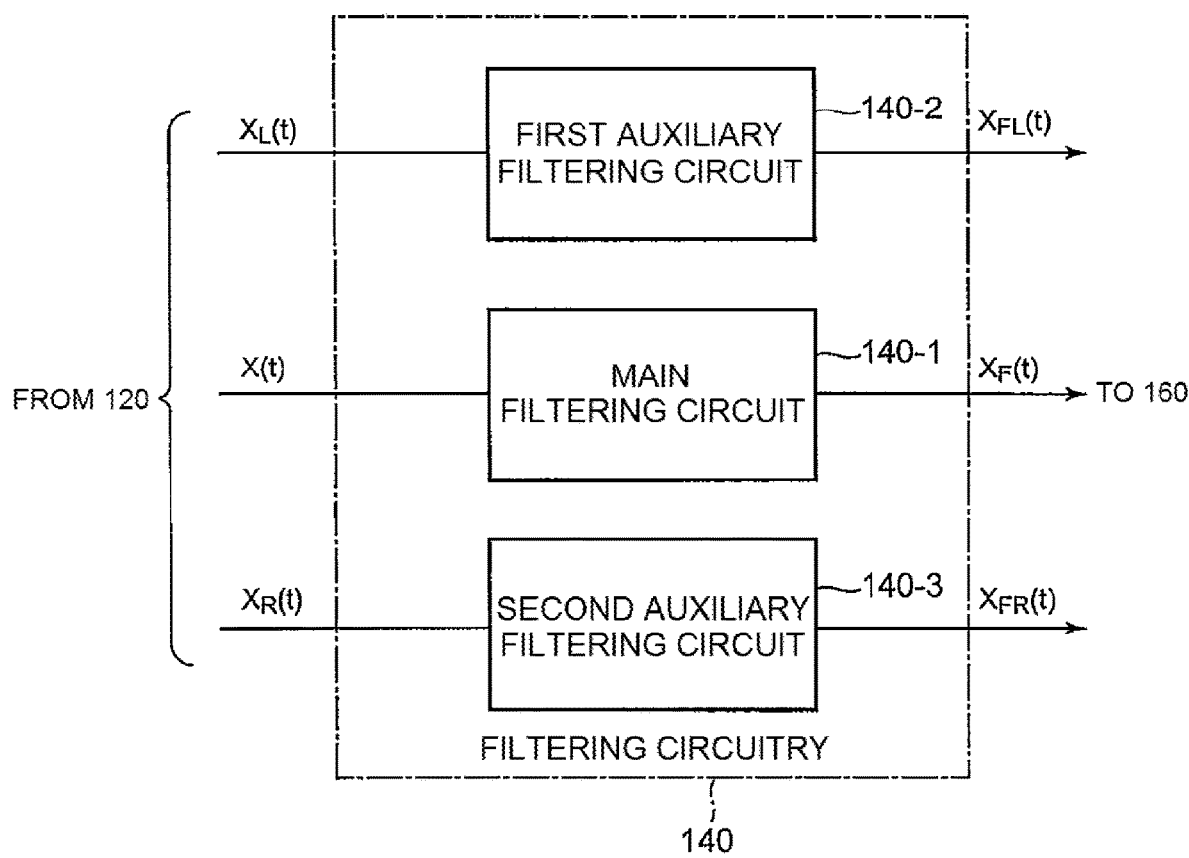
FIG. 6 is a block diagram for illustrating an example of a filtering circuitry for use in the drowsiness estimating device of FIG. 1.

FIG. 6 is a block diagram for illustrating an example of the filtering circuitry 140 in such a case. The filtering circuitry 140 comprises a main filtering circuit 140-1, a first auxiliary filtering circuit 140-2, and a second auxiliary filtering circuit 140-3.

The main filtering circuit 140-1 substitutes the time-series signal X(t) of the eye-openness width with a predetermined main value by filtering it per filtering calculation window width $T_N$ [sec] to produce a substituted signal as the filtered time-series signal $X_F(t)$ of the eye-openness width.

The first auxiliary filtering circuit 140-2 substitutes the time-series signal $X_L(t)$ of the eye-openness width of the left eye 20L with a predetermined first auxiliary value by filtering it per filtering calculation window width $T_N$ [sec] to produce a substituted signal as a filtered time-series signal $X_{FL}(t)$ of the eye-openness width of the left eye 20L.

Likewise, the second auxiliary filtering circuit 140-3 substitutes the time-series signal $X_R(t)$ of the eye-openness width of the right eye 20R with a predetermined second auxiliary value by filtering it per filtering calculation window width $T_N$ [sec] to produce a substituted signal as a filtered time-series signal $X_{FR}(t)$ of the eye-openness width of the right eye 20R.

Although the filtering circuitry 140 comprises three filtering circuits 140-1, 140-2, and 140-3 in the example of FIG. 6, this invention is not limited thereto, and only one of the three filtering circuits may be provided. However, hereinafter, in order to simplify the description, a case where the filtering circuitry 140 comprises only the main filtering circuit 140-1 will be described by way of example.

As filtering processing performed by the filtering circuitry 140, various methods may be adopted.

Next, description will proceed to a specific example of the filtering processing performed by the filtering circuitry 140.

Figure 7:
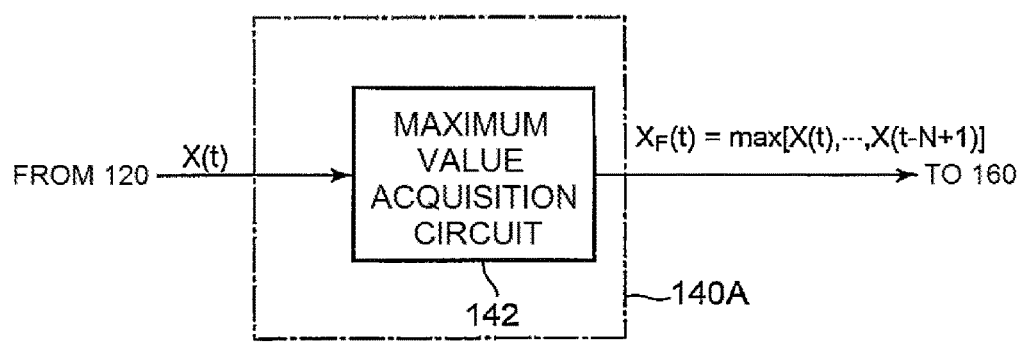
FIG. 7 is a block diagram for illustrating a first example of the filtering circuitry for use in the drowsiness estimating device of FIG. 1.

FIG. 7 is a block diagram for illustrating a first example 140A of the filtering circuitry 140. The filtering circuitry 140A of the first example is applicable to a case where the filtering calculation window width $T_N$ [sec] is at least 0.1 [sec] or more ($T_N \geq 0.1$). This is because a blinking time interval is 0.1 to 0.15 [sec]. That is, the filtering circuitry 140A of the first example is applied to a case where the number N of frames is three or more when the frame rate fs is equal to 30 [frames/sec]. In this example, as shown in FIG. 4, description will be made about a case where the number N of frames is equal to thirty and the filtering calculation window width $T_N$ [sec] is 1 [sec].

The illustrated filtering circuitry 140A comprises a maximum value acquisition circuit 142. The maximum value acquisition circuit 142 acquires, as the predetermined value, a maximum value of the time-series signal X(t) of the eye-openness width by filtering it per filtering calculation window width $T_N$ [sec] and produces the acquired maximum value as the filtered time-series signal $X_F(t)$ of the eye-openness width.

The maximum value acquisition circuit 142 acquires the maximum value of the time-series signal X(t) of the eye-openness width in the filtering calculation window width $T_N$ [sec], as represented by the following Math. 4. Herein, max [ ] is an operator for acquiring the maximum value of elements:

$$X_F(t)=\max [X(t), \ldots ,X(t-N+1)] \qquad [\text{Math.4}]$$

Figure 8:
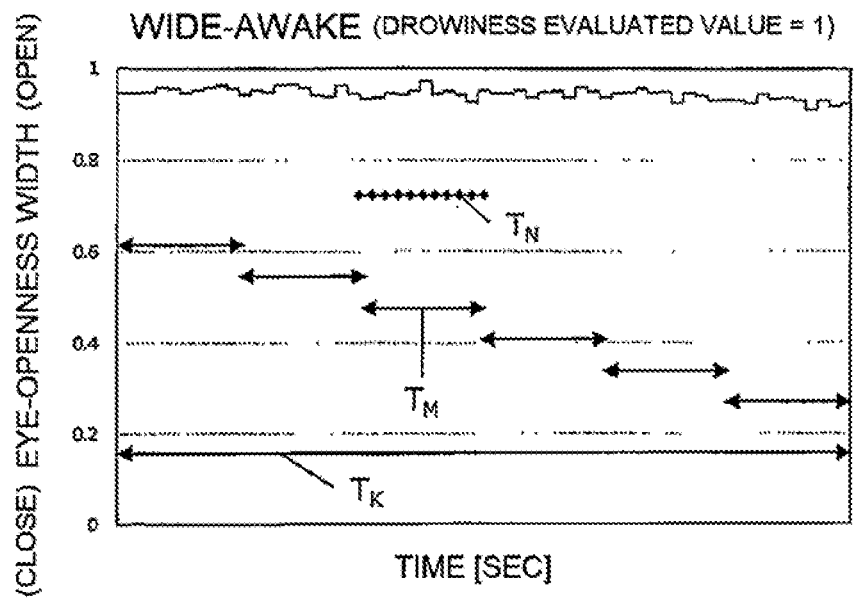
FIG. 8 is a waveform chart for illustrating a time-series signal $X_F(t)$ of the eye-openness width of the subject, after filtering the time-series signal X(t) of the eye-openness width of the subject illustrated in FIG. 4 using the filtering circuitry illustrated in FIG. 7.
Figure 9:
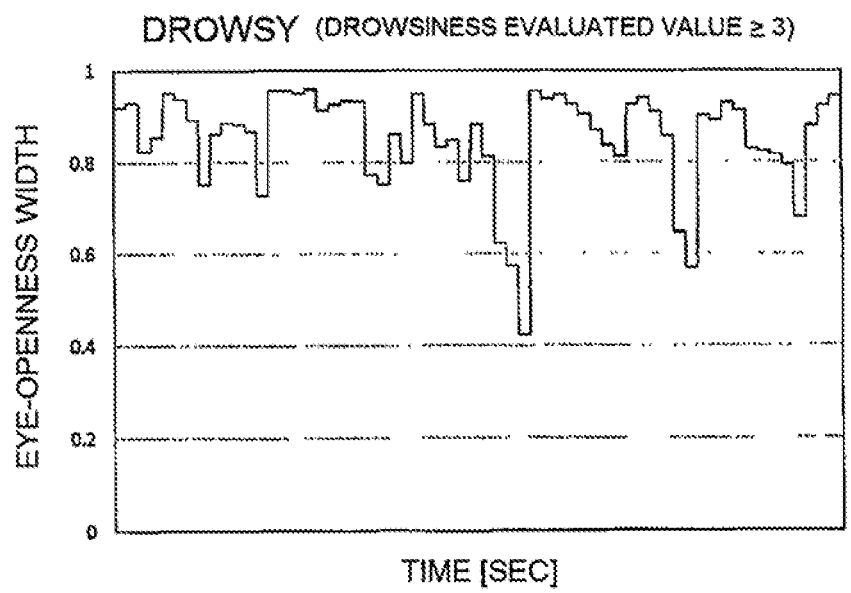
FIG. 9 is a waveform chart for illustrating the time-series signal $X_F(t)$ of the eye-openness width of the subject, after filtering the time-series signal X(t) of the eye-openness width of the subject illustrated in FIG. 5 using the filtering circuitry illustrated in FIG. 7.

FIG. 8 is a waveform chart for illustrating the time-series signal $X_F(t)$ of the eye-openness width of the subject, after filtering the time-series signal X(t) of the eye-openness width of the subject illustrated in FIG. 4 using the filtering circuitry 140A illustrated in FIG. 7. FIG. 9 is a waveform chart for illustrating the time-series signal $X_F(t)$ of the eye-openness width of the subject, after filtering the time-series signal X(t) of the eye-openness width of the subject illustrated in FIG. 5 using the filtering circuitry 140A illustrated in FIG. 7.

The following is understood from comparison between FIG. 8 and FIG. 9. That is, as shown in FIG. 8, it is understood that the eye-openness width is kept constant in a state where the subject 20 is wide-awake. On the other hand, as shown in FIG. 9, it is understood that the eye-openness width is not kept constant in a state where the subject 20 is drowsy.

Figure 10:
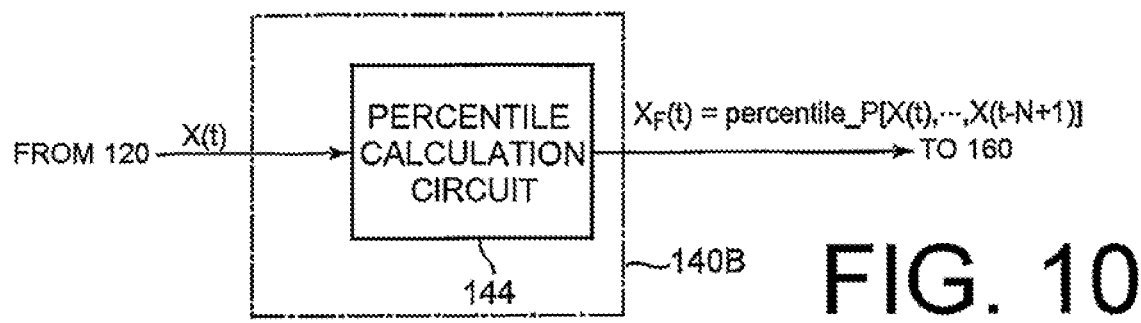
FIG. 10 is a block diagram for illustrating a second example of the filtering circuitry for use in the drowsiness estimating device of FIG. 1.

FIG. 10 is a block diagram for illustrating a second example 140B of the filtering circuitry 140. The filtering circuitry 140B comprises a percentile calculation circuit 144. The percentile calculation circuit 144 calculates, as the above-mentioned predetermined value, a value of a (P−1) P-th percentile of the time-series signal X(t) of the eye-openness width per filtering calculation window width $T_N$ [sec] to produce the value of the (P−1)P-th percentile as the filtered time-series signal $X_F(t)$ of the eye-openness width. Herein, the (P−1)P-th percentile means data at a (P−1)/P-th point from the bottom when data are arranged in an ascending order. Since P=4 in the second example, the (P−1)P-th percentile is a third quartile.

When P is an integer which is two or more, the filtering circuitry 140B of the second example is applicable to a case where the filtering calculation window width $T_N$ [sec] is {0.1+0.1/(P−1)} [sec] or more. This is because the blinking time interval is 0.1 to 0.15 [sec]. In the second example, P is equal to four and the frame rate fs is equal to 30 [frames/sec]. Accordingly, a case where the number N of frames is equal to thirty will be described as a case where the filtering calculation window width $T_N$ [sec] is {0.1+0.1/3} [sec] or the number N of frames is four or more.

The percentile calculation circuit 144 calculates, as the above-mentioned predetermined value, the value of the (P−1)P-th percentile of the time-series signal X(t) of the eye-openness width in the filtering calculation window width $T_N$ [sec], as represented by the following Math. 5. Herein, percentile_P [ ] is an operator for calculating the value of the (P−1)P-th percentile of elements:

$$X_F(t)=\text{percentile\_}P[X(t), \ldots ,X(t-N+1)] \qquad [\text{Math. 5}]$$

Although the percentile calculation circuit 144 calculates, as the above-mentioned predetermined value, the value of the (P−1)P-th percentile of the time-series signal X(t) of the eye-openness width in the filtering calculation window width $T_N$ [sec] in the example being illustrated, the present invention is not limited thereto. For example, the percentile calculation circuit 144 may calculate, as the above-mentioned predetermined value, an average value of the (P−1) P-th percentile and greater values of the time-series signal X(t) of the eye-openness width in the filtering calculation window width $T_N$ [sec].

Figure 11:
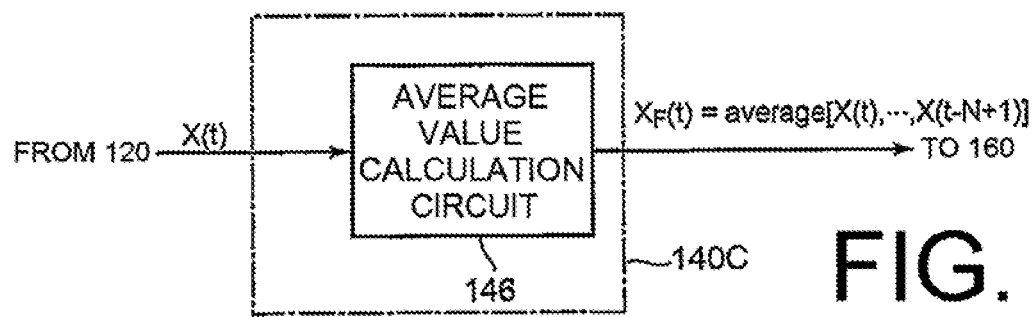
FIG. 11 is a block diagram for illustrating a third example of the filtering circuitry for use in the drowsiness estimating device of FIG. 1.

FIG. 11 is a block diagram for illustrating a third example 140C of the filtering circuitry 140. The filtering circuitry 140C comprises an average value calculation circuit 146. The average value calculation circuit 146 calculates, as the above-mentioned predetermined value, an average value of the time-series signal X(t) of the eye-openness width per filtering calculation window width $T_N$ [sec] to produce the average value as the filtered time-series signal $X_F(t)$ of the eye-openness width.

The filtering circuitry 140C of the third example is applicable to a case where the filtering calculation window width $T_N$ [sec] is a value which is sufficiently larger than 0.1 [sec], for instance, is a value not smaller than 1 [sec] ($T_N \geq 1$). This is because the blinking time interval is 0.1 to 0.15 [sec] and it is intended to remove an influence of blinking by average processing. That is, in the third example, when the frame rate fs is 30 [frames/sec], it is preferable that the number N of frames is thirty or more. In the third example, description will be made of a case where the number N of frames is equal to thirty and the filtering calculation window width $T_N$ [sec] is 1 [sec].

The average value calculation circuit 146 calculates, as the above-mentioned predetermined value, the average value of the time-series signal X(t) of the eye-openness width in the filtering calculation window width $T_N$ [sec], as represented by the following Math. 6. Herein, average [ ] is an operator for calculating the average value of elements:

$$X_F(t)=\text{average}[X(t), \ldots ,X(t-N+1)] \qquad [\text{Math.6}]$$

Figure 12:
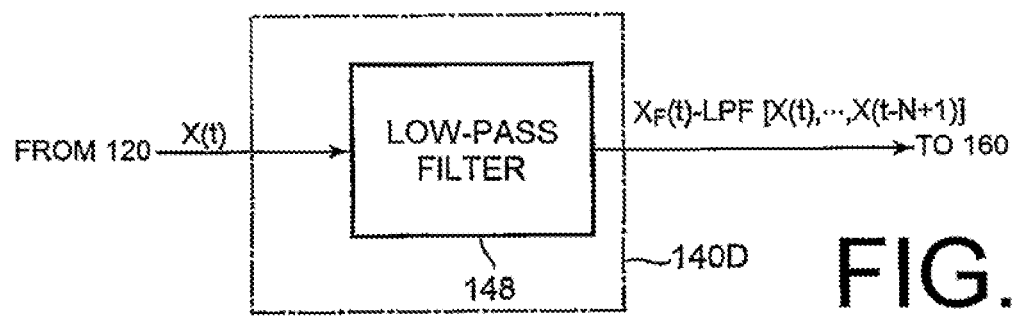
FIG. 12 is a block diagram for illustrating a fourth example of the filtering circuitry for use in the drowsiness estimating device of FIG. 1.

FIG. 12 is a block diagram for illustrating a fourth example 140D of the filtering circuitry 140. The filtering circuitry 140D comprises a low-pass filter (LPF) 148 having a cut-off frequency fc [Hz] which is sufficiently lower than fs. The filtering circuitry 140D produces, as the filtered time-series signal $X_F(t)$ of the eye-openness width, a value obtained after passing through the low-pass filter 148.

When the cut-off frequency is represented by fc [Hz], the filtering circuitry 140D of the fourth example is applicable to a case where fc is sufficiently lower than fs, for example, is not higher than 6 [Hz](fc<<fs). This is because the blinking time interval is 0.1 to 0.15 [sec] or the blinking occurs at 10 to 6.7 Hz, and it is intended to remove the influence of the blinking using the low-pass filter. In the fourth example, description will be made of a case where the cut-off frequency fc [Hz] is equal to 6[Hz].

The low-pass filter 148 selects and produces, as the above-mentioned predetermined value, a value obtained by passing the time-series signal X(t) of the eye-openness width through the low-pass filter 148, as represented by the following Math. 7. Herein, LPF [ ] is an operator for passing elements through the low-pass filter:

$$X_F(t)=\text{LPF}[X(t), \ldots ,X(t-N+1)] \qquad [\text{Math. 7}]$$

Next, description will proceed to the feature calculator 160 in FIG. 1. The feature calculator 160 calculates a feature F(T) from the filtered time-series signal $X_F(t)$ of the eye-openness width per feature calculation window width $T_M$ [sec]. Herein, T is an index of time and is a window number (0, 1, 2, . . . ) of a feature calculation window. Using the feature calculation window width $T_M$ [sec] and the frame rate fs [frames/sec], the number M of frames in the feature calculation window width is represented by $M=T_M \times fs$. In a case of T=0, the feature calculator 160 calculates a feature F(0) using the filtered time-series signal $X_F(t)$ of the eye-openness width having frame numbers t=0 to (M−1). In a case of T=1, the feature calculator 160 calculates a feature F(1) using the filtered time-series signal $X_F(t)$ of the eye-openness width having frame numbers t=M to (2M−1). In a case of T=2, the feature calculator 160 calculates a feature F(2) using the filtered time-series signal $X_F(t)$ of the eye-openness width having fame numbers t=2M to (3M−1). Accordingly, a starting point of feature calculation processing is shifted by T*M. The illustrated feature calculator 160 at least includes a first feature calculation circuit. The first feature calculation circuit calculates a variation in the filtered time-series signal $X_F(t)$ of the eye-openness width within the feature calculation window width $T_M$ [sec] to produce the variation as a first feature F1(T). In a drowsy state, a person is difficult to keep an eyelid constant, and then the above-mentioned variation becomes larger. On the other hand, in a wide-awake state, the person is easy to keep the eyelid constant, and then the above-mentioned variation become smaller. Hereinafter, description will proceed to a specific example of the feature calculator 160.

Figure 13:
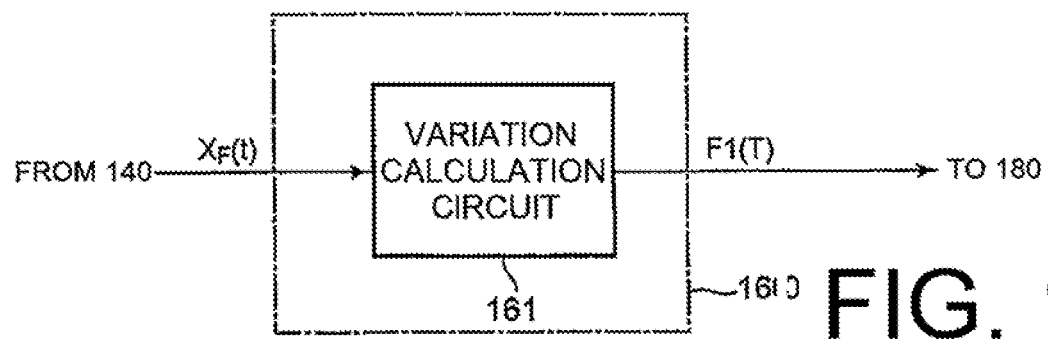
FIG. 13 is a block diagram for illustrating a configuration of a feature calculator for use in the drowsiness estimating device according to the first example embodiment illustrated in FIG. 1.

FIG. 13 is a block diagram for illustrating a configuration of the feature calculator 160. The illustrated feature calculator 160 comprises a variation calculation circuit 161, The variation calculation circuit 161 calculates the variation in the filtered time-series signal $X_F(t)$ of the eye-openness width within the feature calculation window width $T_M$ [sec] to produce the variation as the first feature F1(T). Accordingly, the variation calculation circuit 161 serves as the first feature calculation circuit for calculating and producing the first feature F1(T) from the filtered time-series signal $X_F(t)$ of the eye-openness width.

The variation, namely, the first feature F1(T) is represented by the following Math. 8:

$$F1(T)=V[X_F(T*M+t),\ldots,X_F(T*M+t-M+1)] \quad \text{[Math. 8]}$$

where V[ ] represents an operator for calculating the variation such as a variance, a standard deviation, a difference between the maximum value and the minimum value, and entropy.

Although the filtered time-series signal $X_F(t)$ of the eye-openness width is used in the variation calculation circuit 161 of this example, the above-mentioned filtered time-series signal $X_{FL}(t)$ of the eye-openness width of the left eye 20L and/or the above-mentioned filtered time-series signal $X_{FR}(t)$ of the eye-openness width of the right eye 20R may be used instead. In this case, the variation calculation circuit 161 calculates a variation in the filtered time-series signal $X_{FL}(t)$ of the eye-openness width of the left eye 20L within the feature calculation window width $T_M$ [sec] to produce the variation as the first feature F1(T). Furthermore, the variation calculation circuit 161 calculates a variation in the filtered time-series signal $X_{FR}(t)$ of the eye-openness width of the right eye 20R within the feature calculation window width $T_M$ [sec] to produce the variation as the first feature F1(T).

Figure 14:
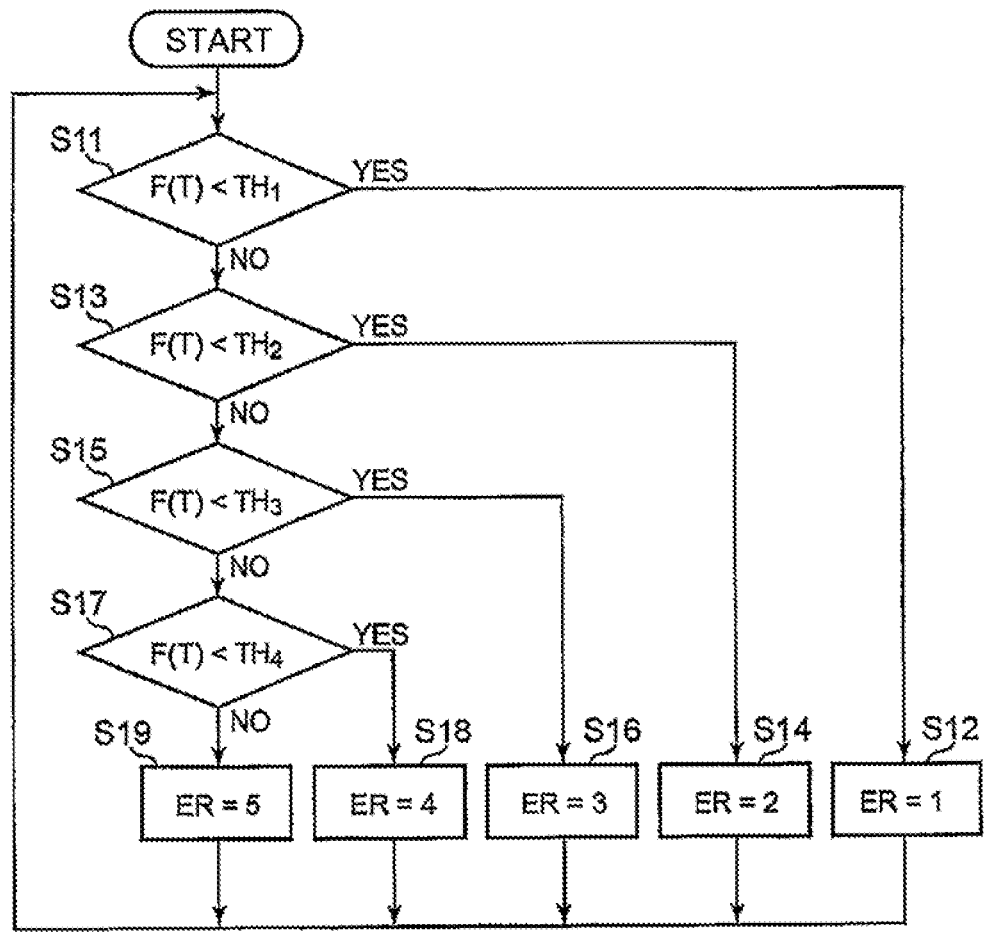
FIG. 14 is a flow chart for illustrating an example of an operation of a drowsiness estimator for use in the drowsiness estimating device of FIG. 1.

Next, description will proceed to the drowsiness estimator 180 in FIG. 1. The drowsiness estimator 180 estimates a drowsiness evaluated value from the feature F(T) to produce an estimated result ER. FIG. 14 is a flow chart for illustrating an example of an operation of the drowsiness estimator 180. Hereinafter, referring to FIG. 14, the operation of the drowsiness estimator 180 will be described.

The illustrated drowsiness estimator 180 is a drowsiness estimator for estimating, from the feature F(T) being the first feature F(T), the above-mentioned drowsiness evaluated values of 1 to 5 to produce the estimated result ER. For this purpose, first through fourth thresholds $TH_1$, $TH_2$, $TH_3$, and $TH_4$ are preliminarily set in the drowsiness estimator 180. Herein, the first through the fourth thresholds $TH_1$, $TH_2$, $TH_3$, and $TH_4$ have values which become larger in this order. That is, $TH_1 < TH_2 < TH_3 < TH_4$.

First, the drowsiness estimator 180 compares the feature F(T) with the first threshold $TH_1$ (Step S11). If the feature F(T) is smaller than the first threshold $TH_1$ (YES in the Step S11), the drowsiness estimator 180 determines that the subject 20 is "not drowsy at all" and produces, as the estimated result ER, the drowsiness evaluated value of "1" (Step S12). This indicates that the subject 20 is wide-awake and the eye-openness width is kept constant, as shown in FIG. 8.

If the feature F(T) is not smaller than the first threshold $TH_1$ (NO in the Step S11), the drowsiness estimator 180 compares the feature F(T) with the second threshold $TH_2$ (Step S13). If the feature F(T) is smaller than the second threshold $TH_2$ (YES in the Step S13), the drowsiness estimator 180 determines that the subject 20 is "slightly drowsy" and produces, as the estimated result ER, the drowsiness evaluated value of "2" (Step S14).

If the feature F(T) is not smaller than the second threshold $TH_2$ (NO in the Step S13), the drowsiness estimator 180 compares the feature F(T) with the third threshold $TH_3$ (Step S15). If the feature F(T) is smaller than the third threshold $TH_3$ (YES in the Step S15), the drowsiness estimator 180 determines that the subject 20 is "drowsy" and produces, as the estimated result ER, the drowsiness evaluated value of "3" (Step S16). This indicates that the subject 20 is drowsy and the eye-openness width is not kept constant, as shown in FIG. 9.

If the feature F(T) is not smaller than the third threshold $TH_3$ (NO in the Step S15), the drowsiness estimator 180 compares the feature F(T) with the fourth threshold $TH_4$ (Step S17). If the feature F(T) is smaller than the fourth threshold $TH_4$ (YES in the Step S17), the drowsiness estimator 180 determines that the subject 20 is "very drowsy" and produces, as the estimated result ER, the drowsiness evaluated value of "4" (Step S18).

If the feature F(T) is not smaller than the fourth threshold $TH_4$ (NO in the Step S17), the drowsiness estimator 180 determines that the subject 20 is "extremely drowsy" and produces, as the estimated result ER, the drowsiness evaluated value of "5" (Step S19).

As described above, the drowsiness estimator 180 estimates, from the feature F(T), the drowsiness evaluated values of 1 to 5 to produce the estimated result ER. After producing the estimated result ER, the drowsiness estimator 180 turns back to processing of the Step S11.

Although the drowsiness estimator 180 compares the feature F(T) with the first through the fourth thresholds $TH_1$ to $TH_4$ in an ascending order of values in this example, the present invention is not limited thereto. That is, the drowsiness estimator 180 may compare the feature F(T) with the fourth through the first thresholds $TH_4$ to $TH_1$ in a descending order of values.

Although the drowsiness estimator 180 produces, as the estimated result ER, the drowsiness evaluated values of five levels of 1 to 5 in this example, the present invention is not limited thereto. For instance, the drowsiness estimator 180 may estimate, from the feature F(T), only two states, in which the subject 20 is "not drowsy" and is "drowsy", to produce only the two states as the estimated result ER. In this case, only one threshold $TH_0$ is set in the drowsiness estimator 180. As the one threshold $TH_0$, for example, the above-mentioned third threshold $TH_3$ may be used, but the present invention is not limited thereto. It is a matter of course that, depending on circumstances, various thresholds may be selected. Furthermore, the drowsiness evaluated values are discrete values. However, since the drowsiness is normally a continuous value, the continuous value may be estimated by treating the drowsiness as a regression problem, not a classification problem as described above. In this case, instead of the thresholds, parameters of a regression equation may be set by preliminarily learning, for example, a and b in ER=aF(T)+b in a case of simple linear regression. As a matter of course, in the above-mentioned classification problem and the regression program, not only a linear method but also various methods such as machine learning methods commonly frequently used, for example, a support vector machine, a random forest, or a neural network is applicable upon learning various parameters.

[Description of Operation]

Figure 15:
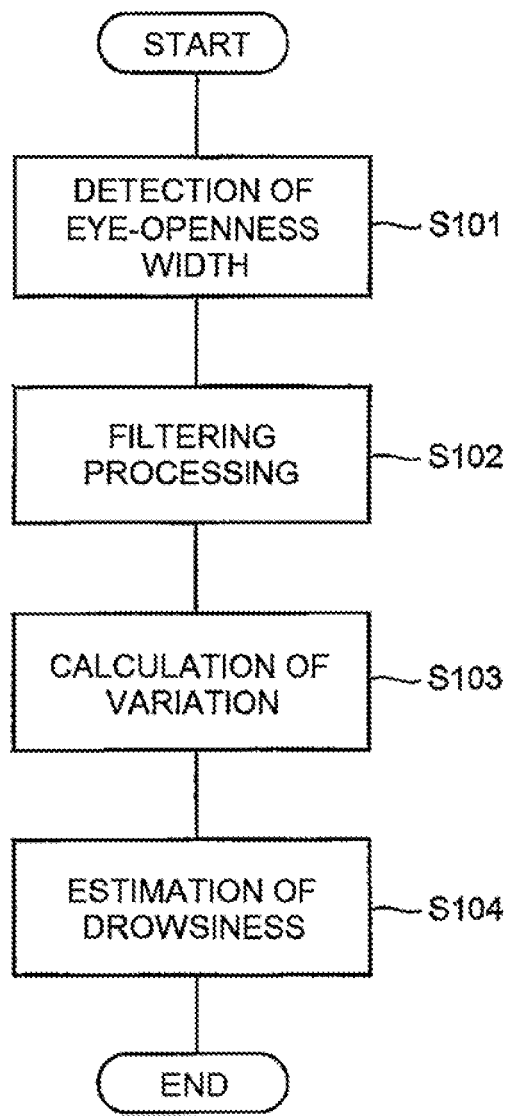
FIG. 15 is a flow chart for use in describing an operation of the drowsiness estimating device according to the first example embodiment illustrated in FIG. 1.

Next, referring to a flow chart of FIG. 15, description will proceed to an operation of the drowsiness estimating device 100 according to the first example embodiment.

First, the eye-openness width detector 120 detects the eye-openness width from the moving image signal V(t) to produce the time-series signal X(t) of the eye-openness width (Step S101).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S102).

Subsequently, the feature calculator 160 calculates the variation in the filtered time-series signal $X_F(t)$ of the eye-openness width within the feature calculation window width $T_M$ [sec] to produce the variation as the first feature F1(T) (Step S103).

Finally, the drowsiness estimator 180 estimates the drowsiness evaluated value of the subject 20 from the first feature F1(T) to produce the estimated result ER (Step S104).

[Description of Effect]

Next, an effect of the first example embodiment will be described.

According to the first example embodiment of the present invention, it is possible to estimate the drowsiness with high accuracy independent of various conditions such as a time window width for estimating the drowsiness and/or a sampling rate of data of the eye-openness width. First reason is that the blinking is not used as a feature for drowsiness estimation. It is said that the number of times of the blinking is fifteen to twenty per one minute. In order to capture the feature of the changes in the number of times of the blinking, changes in intervals of the blinking, and so on, it is necessary to extract the feature in the time window of at least about one minute. However, the present invention uses a remaining large part of data of the eye-openness width except blinking sections. It is therefore possible to estimate the drowsiness with high accuracy even if the time window width is set to be shorter than one minute (e.g. ten seconds) or to be longer (e.g. three minutes). Further, as regards the sampling rate of the data of the eye-openness width, it is necessary to set a high sampling rate (e.g. 10 frames/sec or more) in order to calculate the feature by capturing the blinking of 0.1 to 0.15 sec. In the present invention, however, it is not necessary to capture the blinking. It is therefore possible to estimate the drowsiness with high accuracy even if the sampling rate is 5 frames/sec or 3 frames/sec. To estimate the drowsiness with high accuracy at a low frame rate directly influences required specifications of a camera and required specifications of a CPU, namely, directly influences a system cost, and is therefore very important industrially. A second reason why the present invention can obtain the effect is that, upon eliminating the signal changes due to the blinking by the filtering circuitry 140 of the present invention, the parameter such as the filtering calculation window width is set based on a time length (0.1 to 0.15 sec) of the blinking of a person. Therefore, it is possible to reliably eliminate an influence of the signal changes due to the blinking and it is possible to achieve high-accuracy drowsiness estimation because the parameter value is learned data, namely, is independent of the person. Furthermore, a third reason is because the time-series signal of the eye-openness width is filtered so as to eliminate the signal changes due to the blinking of the subject therefrom, the variation being the first feature is calculated from the filtered time-series signal of the eye-openness width, and the drowsiness evaluated value is estimated from the first feature. By calculating the variation from the filtered time series signal of the eye-openness width, it is possible to reliably capture any change in the drowsiness even in case of slight drowsiness.

Each part of the drowsiness estimating device 100 may be implemented by a combination of hardware and software. In a form in which the hardware and the software are combined, the respective parts are implemented as various kinds of means by developing a drowsiness estimating program in a RAM (random access memory) and making hardware such as a control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned first example embodiment with a different expression, it is possible to implement the example embodiment by making a computer to be operated as the drowsiness estimating device 100 act as the eye-openness width detector 120, the filtering circuitry 140, the feature calculator 160, and the drowsiness estimator 180 according to the drowsiness estimating program developed in the RAM.

Second Example Embodiment

Figure 16:
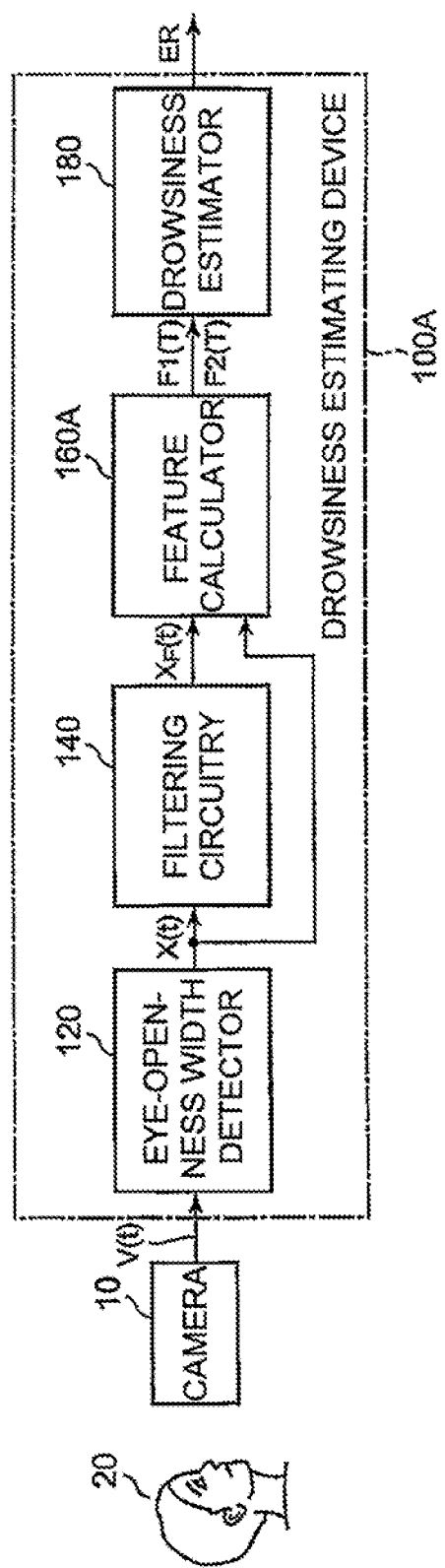
FIG. 16 is a block diagram for illustrating a configuration of a drowsiness estimating device according to a second example embodiment of this invention.

FIG. 16 is a block diagram for illustrating a configuration of a drowsiness estimating device 100A according to a second example embodiment of this invention. The illustrated drowsiness estimating device 100A may be implemented by a computer which operates under program control.

The illustrated drowsiness estimating device 100A is similar in structure and operation to the drowsiness estimating device 100 illustrated in FIG. 1 except that the feature calculator is different in structure as will later be described. The feature calculator is therefore depicted by the reference numeral 160A. The same reference numerals are assigned to parts similar in function to those illustrated in FIG. 1, and description thereof will be omitted in order to simplify the description.

Figure 17:
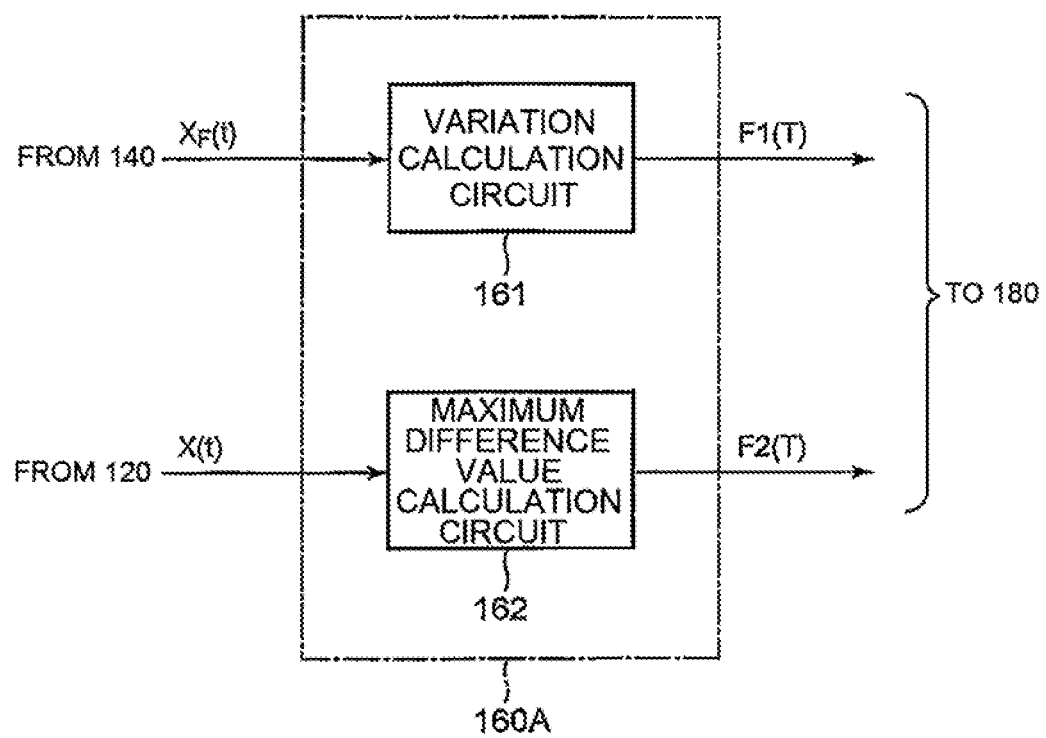
FIG. 17 is a block diagram for illustrating a configuration of a feature calculator for use in the drowsiness estimating device according to the second example embodiment illustrated in FIG. 16.

FIG. 17 is a block diagram for illustrating a configuration of the feature calculator 160A. The illustrated feature calculator 160A is similar in structure and operation to the feature calculator 160 illustrated in FIG. 13 except that a maximum difference value calculation circuit 162 is further provided. Accordingly, the feature calculator 160A comprises the variation calculation circuit 161 and the maximum difference value calculation circuit 162.

The maximum difference value calculation circuit 162 calculates absolute values of inter-frame differences of the time-series signal X(t) of the eye-openness width (that will be called "inter-frame differences" hereinafter), calculates a maximum value of the inter-frame differences within the feature calculation window width ($T_M$) [sec], and produces the maximum value as a second feature F2(T). Accordingly, the maximum difference value calculation circuit 162 serves as a second feature calculation circuit for calculating and producing the second feature F2(T) from the time-series signal X(t) of the eye-openness width. The maximum value of the absolute values of the inter-frame differences has a small value in the drowsy state and a large value in the wide-awake state, and is therefore useful in drowsiness estimation.

The maximum value of the inter-frame differences, namely, the second feature F2(T) is represented by the following Math. 9:

$$F2(T)=1-\max\left[|X(T^*M+t)-X(T^*M+t-1)|,\ldots,|X(T^*M+t-M+1)-X(T^*M+t-M+1-1)|\right]$$ [Math. 9]

Herein, a reason why "1−max [ ]" is used is to make the value be smaller as the drowsiness is slighter, like the other features.

Although the time-series signal X(t) of the eye-openness width is used in the maximum difference value calculation circuit 162 of this example, the above-mentioned time-series signal $X_L$(t) of the eye-openness width of the left eye 20L and/or the above-mentioned time-series signal $X_R$(t) of the eye-openness width of the right eye 20R may be used instead. In this case, the maximum difference value calculation circuit 162 calculates a maximum value of inter-frame differences in the time-series signal $X_L$(t) of the eye-openness width of the left eye 20L within the feature calculation window width $T_M$ [sec] to produce the maximum value as the second feature F2(T). Furthermore, the maximum difference value calculation circuit 162 calculates a maximum value of inter-frame differences in the time-series signal $X_R$(t) of the eye-openness width of the right eye 20R within the feature calculation window width $T_M$ [sec] to produce the maximum value as the second feature F2(T).

[Description of Operation]

Figure 18:
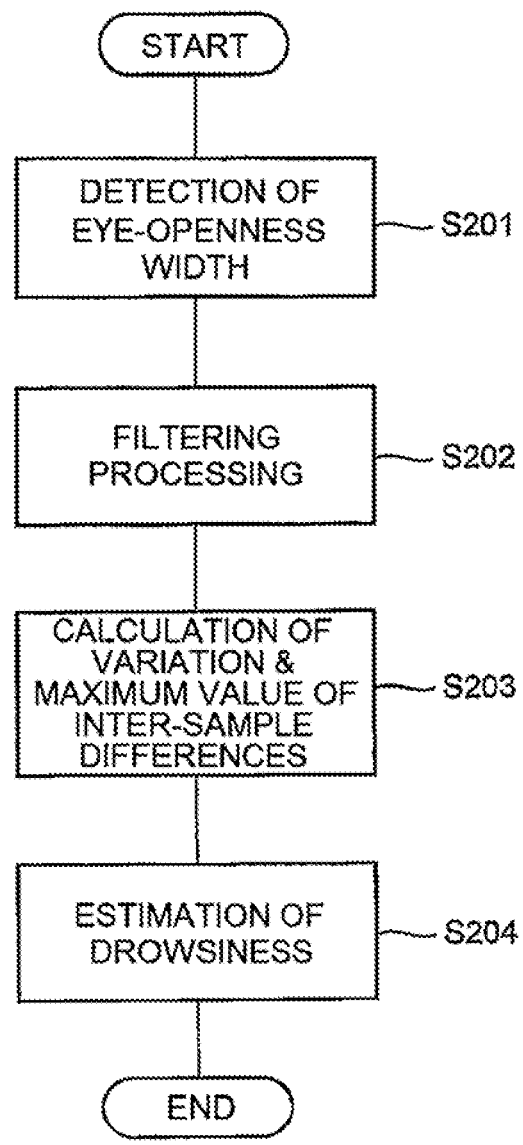
FIG. 18 is a flow chart for use in describing an operation of the drowsiness estimating device according to the second example embodiment illustrated in FIG. 16.

Next, referring to a flow chart of FIG. 18, description will proceed to an operation of the drowsiness estimating device 100A according to the second example embodiment.

First, the eye-openness width detector 120 detects the eye-openness width from the moving image signal V(t) to produce the time-series signal X(t) of the eye-openness width (Step S201).

Next, the filtering circuitry 140 filters the time-series signal X(t) of the eye-openness width so as to eliminate signal changes due to blinking of the subject 20 therefrom to produce the filtered time-series signal $X_F$(t) of the eye-openness width (Step S202).

Subsequently, the feature calculator 160A calculates the variation in the filtered time-series signal $X_F$(t) of the eye-openness width within the feature calculation window width $T_M$ [sec] to produce the variation as the first feature F1(T), and calculates the maximum value of the inter-frame differences in the time-series signal X(t) of the eye-openness width within the feature calculation window width $T_M$ [sec] to produce the maximum value as the second feature F2(T) (Step S203).

Finally, the drowsiness estimator 180 estimates the drowsiness evaluated value of the subject 20 from the first feature F1(T) and the second feature F2(T) to produce the estimated result ER (Step S204).

[Description of Effect]

Next, an effect of the second example embodiment will be described.

According to the second example embodiment of the present invention, it is possible to estimate the drowsiness with higher accuracy as compared with the first example embodiment. This is because information usable in drowsiness estimation increases by adding, as the second feature, the maximum value of the absolute values of the inter-frame differences of the eye-openness width.

Each part of the drowsiness estimating device 100A may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned second example embodiment with a different expression, it is possible to implement the example embodiment by making a computer to be operated as the drowsiness estimating device 100A act as the eye-openness width detector 120, the filtering circuitry 140, the feature calculator 160A, and the drowsiness estimator 180 according to the drowsiness estimating program developed in the RAM.

Third Example Embodiment

Figure 19:
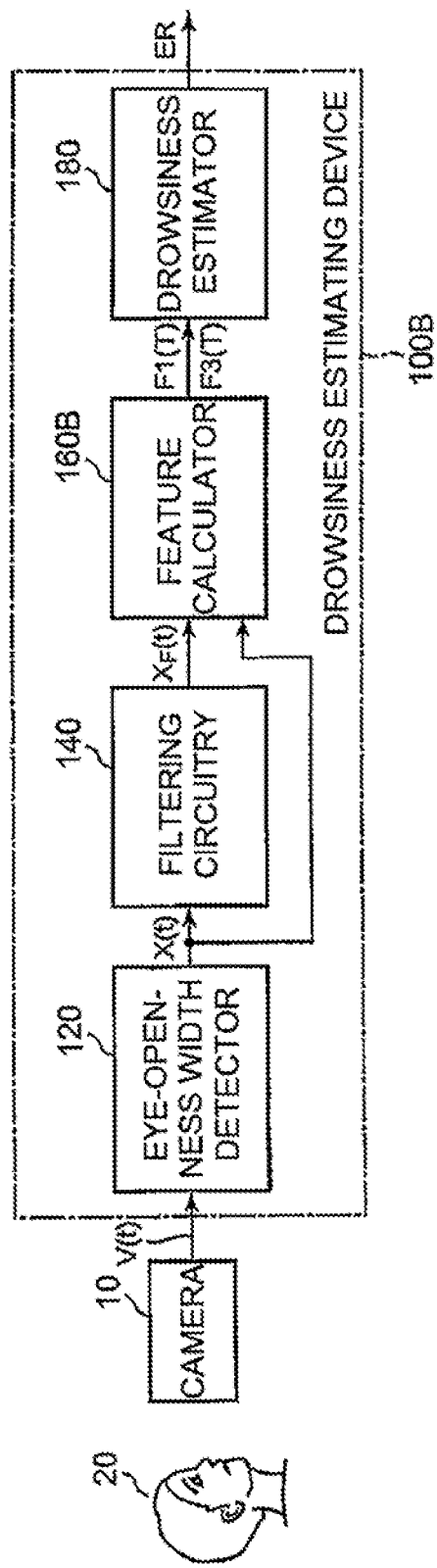
FIG. 19 is a block diagram for illustrating a configuration of a drowsiness estimating device according to a third example embodiment of this invention.

FIG. 19 is a block diagram for illustrating a configuration of a drowsiness estimating device 100B according to a third example embodiment of this invention. The illustrated drowsiness estimating device 100B may be implemented by a computer which operates under program control.

The illustrated drowsiness estimating device 100B is similar in structure and operation to the drowsiness estimating device 100 illustrated in FIG. 1 except that the feature calculator is different in structure as will later be described. The feature calculator is therefore depicted by the reference numeral 160B. The same reference numerals are assigned to parts similar in function to those illustrated in FIG. 1, and description thereof will be omitted in order to simplify the description.

Figure 20:
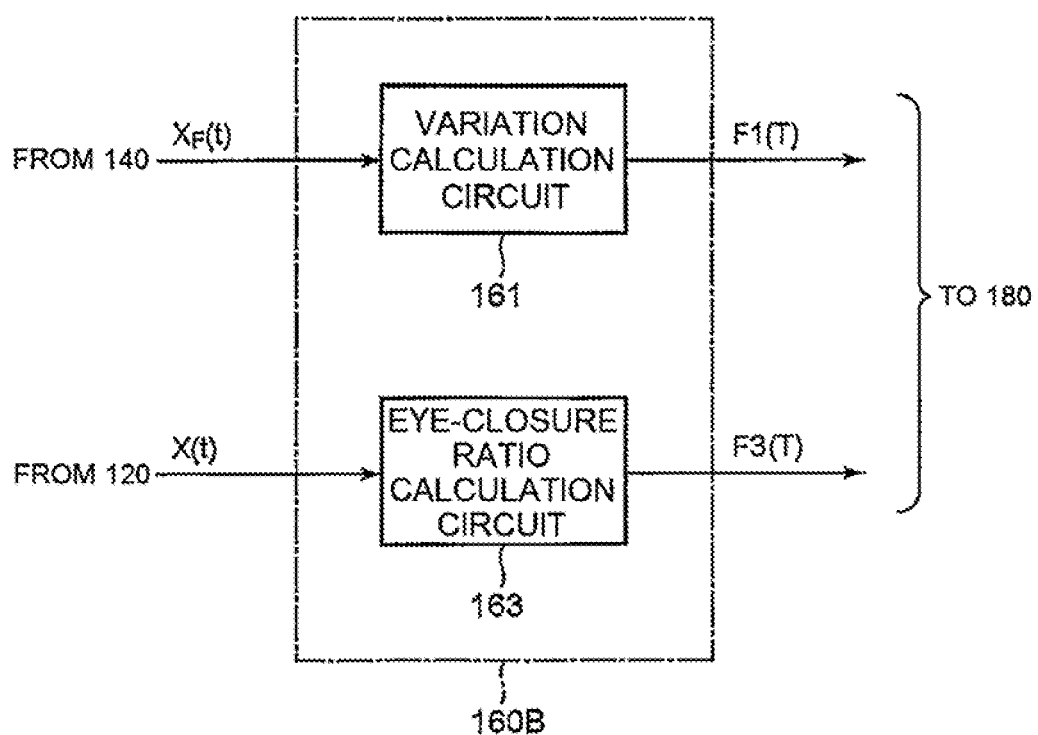
FIG. 20 is a block diagram for illustrating a configuration of a feature calculator for use in the drowsiness estimating device according to the third example embodiment illustrated in FIG. 19.

FIG. 20 is a block diagram for illustrating a configuration of the feature calculator 160B. The illustrated feature calculator 160B is similar in structure and operation to the feature calculator 160 illustrated in FIG. 13 except that an eye-closure ratio calculation circuit 163 is further provided. Accordingly, the feature calculator 160B comprises the variation calculation circuit 161 and the eye-closure ratio calculation circuit 163.

The eye-closure ratio calculation circuit 163 detects eye closure from the time-series signal X(t) of the eye-openness width, calculates an eye-closure ratio within the feature calculation window width ($T_M$) [sec], and produces the eye-closure ratio as a third feature F3(T). Accordingly, the eye-closure ratio calculation circuit 163 serves as a third feature calculation circuit for calculating and producing the third feature F3(T) from the time-series signal X(t) of the eye-openness width. The eye-closure ratio has a large value in the drowsy state and a small value in the wide-awake state, and is therefore useful in drowsiness estimation.

$$F3(T)=C/M \qquad \text{[Math. 10]}$$

where C represents the number of elements below an eye-closure decision threshold (e.g. 0.5) among [X(T*M+t), . . . , X(T*M+t−M+1)].

For details of the eye-closure ratio, for example, see the above-mentioned Non-Patent Literature 2.

Although the time-series signal X(t) of the eye-openness width is also used in the eye-closure ratio calculation circuit 163 of this example, the above-mentioned time-series signal $X_L(t)$ of the eye-openness width of the left eye 20L and/or the above-mentioned time-series signal $X_R(t)$ of the eye-openness width of the right eye 20R may be used instead. In this case, the eye-closure ratio calculation circuit 163 calculates an eye-closure ratio in the time-series signal $X_L(t)$ of the eye-openness width of the left eye 20L within the feature calculation window width $T_M$ [sec] to produce the eye-closure ratio as the third feature F3(T). Furthermore, the eye-closure ratio calculation circuit 163 calculates an eye-closure ratio in the time-series signal $X_R(t)$ of the eye-openness width of the right eye 20R within the feature calculation window width $T_M$ [sec] to produce the eye-closure ratio as the third feature F3(T). Furthermore, the eye-closure ratio calculation circuit calculates an eye-closure ratio upon simultaneous eye closure in both of the time-series signal $X_L(t)$ of the eye-openness width of the left eye 20L and the time-series signal $X_R(t)$ of the eye-openness width of the right eye 20R to produce the eye-closure ratio as the third feature F3(T). In addition, the eye-closure ratio calculation circuit calculates an eye-closure ratio in the time-series signal $X_L(t)$ of the eye-openness width of the left eye 20L and an eye-closure ratio in the time-series signal $X_R(t)$ of the eye-openness width of the right eye 20R, respectively, to produce the third feature F3(T)=[the eye-closure ratio of $X_L(t)$, the eye-closure ratio of $X_R(t)$] including those ratios as elements. Furthermore, the eye-closure ratio calculation circuit calculates a plurality of eye-closure ratios using a plurality of eye-closure decision thresholds (e.g. 0.5 and 0.8) to produce the third feature F3(T)=[the eye-closure ratio in a case of the eye-closure decision threshold of 0.5, the eye-closure ratio in a case of the eye-closure decision threshold of 0.8] including those ratios as elements.

[Description of Operation]

Figure 21:
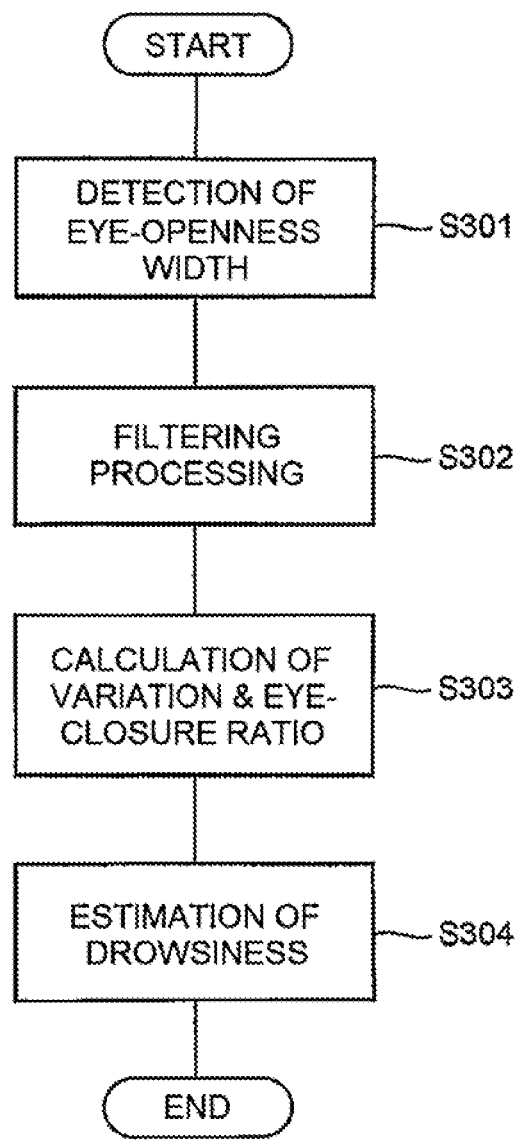
FIG. 21 is a flow chart for use in describing an operation of the drowsiness estimating device according to the third example embodiment illustrated in FIG. 19.

Next, referring to a flow chart of FIG. 21, description will proceed to an operation of the drowsiness estimating device 100B according to the third example embodiment.

First, the eye-openness width detector 120 detects the eye-openness width from the moving image signal V(t) to produce the time-series signal X(t) of the eye-openness width (Step S301).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S302).

Subsequently, the feature calculator 160B calculates the variation in the filtered time-series signal $X_F(t)$ of the eye-openness width within the feature calculation window width $T_M$ [sec] to produce the variation as the first feature F1(T), and calculates the eye-closure ratio in the time-series signal X(t) of the eye-openness width within the feature calculation window width $T_M$ [sec] to produce the eye-closure ratio as the third feature F3(T)(Step S303).

Finally, the drowsiness estimator 180 estimates the drowsiness evaluated value of the subject 20 from the first feature F1(T) and the third feature F3(T) to produce the estimated result ER (Step S304).

[Description of Effect]

Next, an effect of the third example embodiment will be described.

According to the third example embodiment of the present invention, it is possible to estimate the drowsiness with higher accuracy as compared with the first example embodiment. This is because information usable in drowsiness estimation increases by adding, as the third feature, the eye-closure ratio. Specifically, in a perfectly sleeping state, it is difficult to estimate a sleeping state using only the first feature. On the other hand, in the perfectly sleeping state, the eye-closure ratio is obviously high. Therefore, by adding the third feature, it is possible to estimate the drowsiness with high accuracy, including the perfectly sleeping state. It is noted that, only with the third feature, it is difficult to estimate slight drowsiness with the small eye-closure ratio. Therefore, an effect of using a combination of the first feature and the third feature is very high.

Each part of the drowsiness estimating device 100B may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. Byway of example, the recoding medium may be an optical disc, a magnetic disk, a semiconductor memory device, a hard disk, or the like.

Explaining the above-mentioned third example embodiment with a different expression, it is possible to implement the example embodiment by making a computer to be operated as the drowsiness estimating device 100B act as the eye-openness width detector 120, the filtering circuitry 140, the feature calculator 160B, and the drowsiness estimator 180 according to the drowsiness estimating program developed in the RAM.

Fourth Example Embodiment

Figure 22:
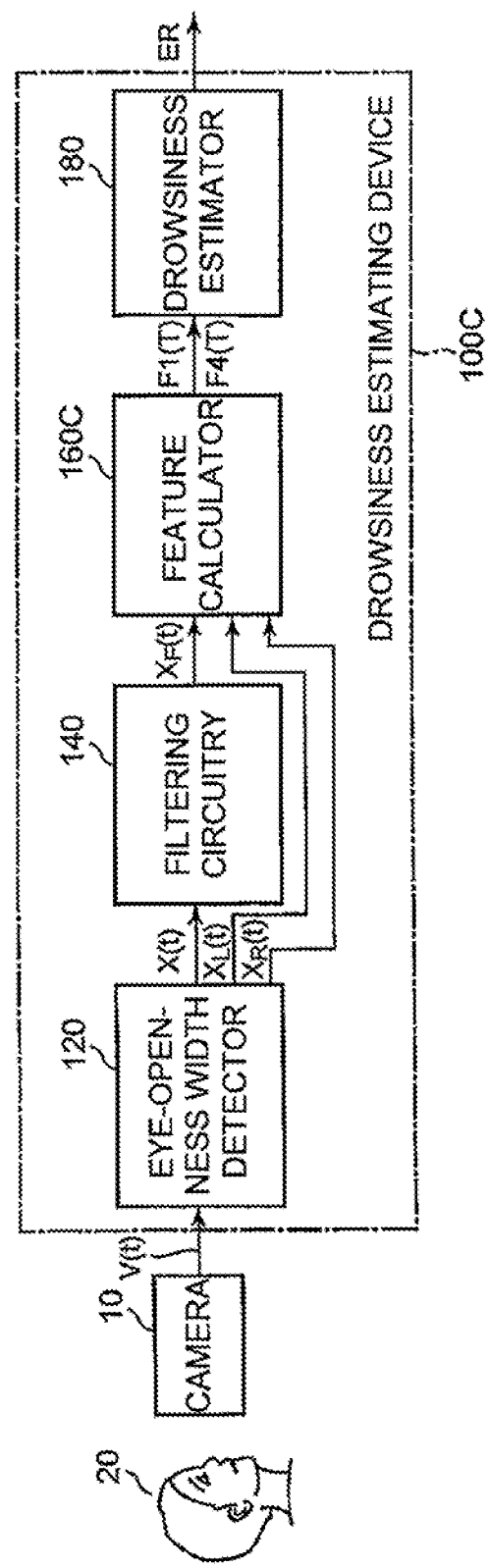
FIG. 22 is a block diagram for illustrating a configuration of a drowsiness estimating device according to a fourth example embodiment of this invention.

FIG. 22 is a block diagram for illustrating a configuration of a drowsiness estimating device 100C according to a fourth example embodiment of this invention. The illustrated drowsiness estimating device 100C may be implemented by a computer which operates under program control.

The illustrated drowsiness estimating device 100C is similar in structure and operation to the drowsiness estimating device 100 illustrated in FIG. 1 except that the feature calculator is different in structure as will later be described. The feature calculator is therefore depicted by the reference numeral 160C. The same reference numerals are assigned to parts similar in function to those illustrated in FIG. 1, and description thereof will be omitted in order to simplify the description.

Figure 23:
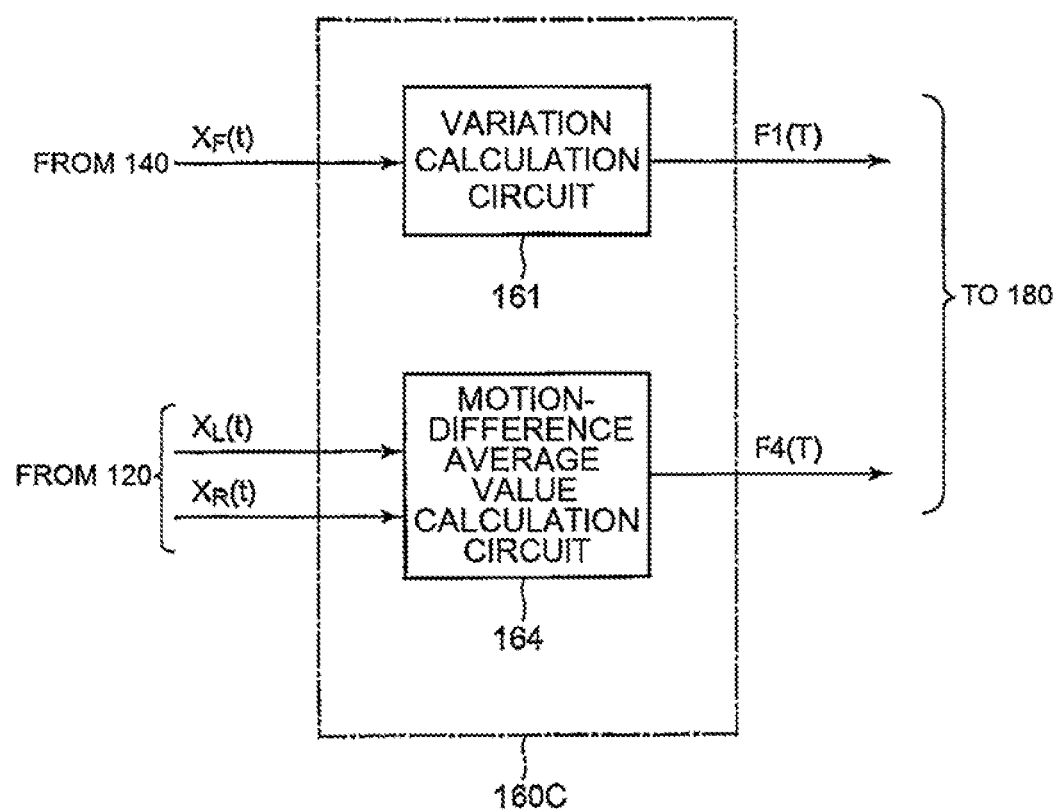
FIG. 23 is a block diagram for illustrating a configuration of a feature calculator for use in the drowsiness estimating device according to the fourth example embodiment illustrated in FIG. 22.

FIG. 23 is a block diagram for illustrating a configuration of the feature calculator 160C. The illustrated feature calculator 160C is similar in structure and operation to the feature calculator 160 illustrated in FIG. 13 except that a motion-difference average calculation circuit 164 is further provided. Accordingly, the feature calculator 160C comprises the variation calculation circuit 161 and the motion-difference average calculation circuit 164.

The motion-difference average value calculation circuit 164 calculates absolute values of motion differences between the time-series signal $X_L(t)$ of the eye-openness width of the left eye 20L and the time-series signal $X_R(t)$ of the eye-openness width of the right eye 20R (that will be called "motion differences" hereinafter), calculates an average value of the motion differences within the feature calculation window width $(T_M)$ [sec], and produces the average value of the motion differences as a fourth feature F4(T). Accordingly, the motion-difference average value calculation circuit 164 serves as a fourth feature calculation circuit for calculating and producing the fourth feature F4(T) from the time-series signal X(t) of the eye-openness width. The average value of the motion differences has a large value in the drowsy state and has a small value in the wide-awake state, and is therefore useful in drowsiness estimation.

The average value of the motion differences, namely, the fourth feature F4(T) is represented by the following Math. 11:

$$F4(T)=\text{average}[|\{X_L(T^*M+t)-X_L(T^*M+t-1)\}-\{X_R(T^*M+t)-X_R(T^*M+t-1)\}|, \ldots, |\{X_L(T^*M+t-M+1)-X_L(T^*M+t-M+1-1)\}-\{X_R(T^*M+t-M+1)-X_R(T^*M+t-M+1-1)\}|]$$  [Math. 11]

[Description of Operation]

Figure 24:
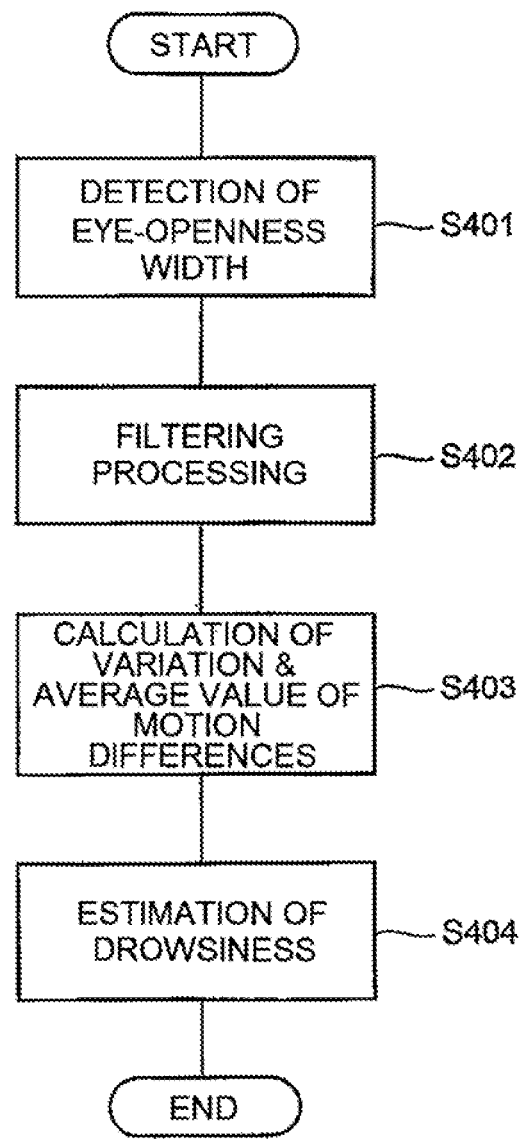
FIG. 24 is a flow chart for use in describing an operation of the drowsiness estimating device according to the fourth example embodiment illustrated in FIG. 22.

Next, referring to a flow chart of FIG. 24, description will proceed to an operation of the drowsiness estimating device 100C according to the fourth example embodiment.

First, the eye-openness width detector 120 detects the eye-openness width from the moving image signal V(t) to produce the time-series signal X(t) of the eye-openness width, the time-series signal $X_L(t)$ of the eye-openness width of the left eye 20L, and the time-series signal $X_R(t)$ of the eye-openness width of the right eye 20R (Step S401).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S402).

Subsequently, the feature calculator 160C calculates the variation in the filtered time-series signal $X_F(t)$ of the eye-openness width within the feature calculation window width $T_M$ [sec] to produce the variation as the first feature F1(T), and calculates the motion differences of the eye-openness width between the left eye and the right eye within the feature calculation window width $T_M$ [sec] to produce the average value of the motion differences as the fourth feature F4(T) (Step S403).

Finally, the drowsiness estimator 180 estimates the drowsiness evaluated value of the subject 20 from the first feature F1(T) and the fourth feature F4(T) to produce the estimated result ER (Step S404).

[Description of Effect]

Next, an effect of the fourth example embodiment will be described.

According to the fourth example embodiment of the present invention, it is possible to estimate the drowsiness with higher accuracy as compared with the first example embodiment. This is because information usable in drowsiness estimation increases by adding, as the fourth feature, the average value of the motion differences. By appropriately capturing different motions of the right eye and the left eye, accuracy of the drowsiness estimation is improved.

Each part of the drowsiness estimating device 100C may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned fourth example embodiment with a different expression, it is possible to implement the example embodiment by making a computer to be operated as the drowsiness estimating device 100C act as the eye-openness width detector 120, the filtering circuitry 140, the feature calculator 160C, and the drowsiness estimator 180 according to the drowsiness estimating program developed in the RAM.

Fifth Example Embodiment

Figure 25:
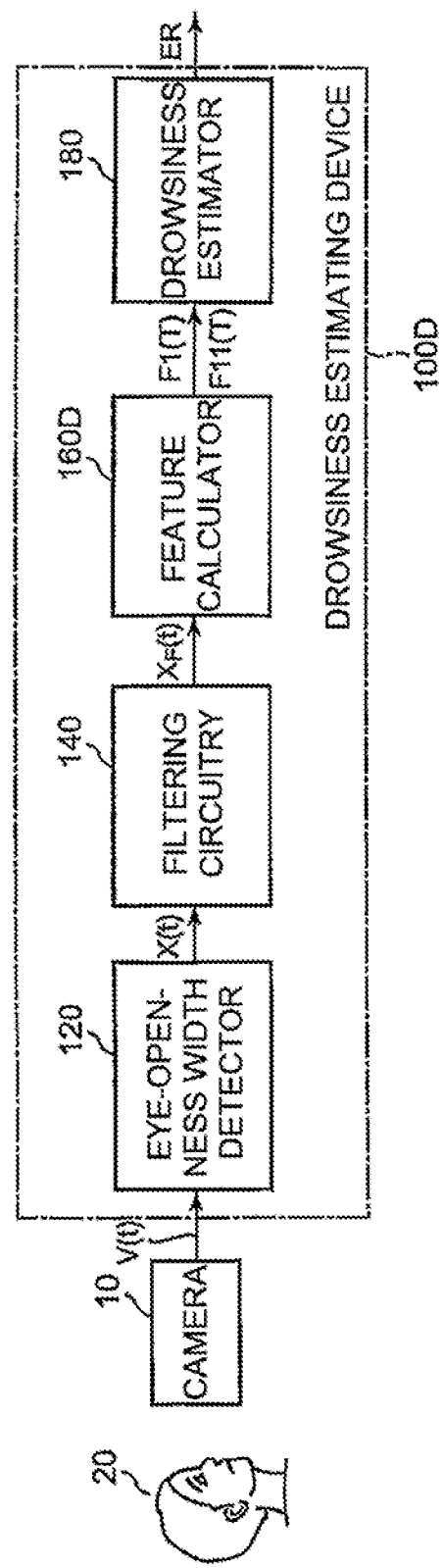
FIG. 25 is a block diagram for illustrating a configuration of a drowsiness estimating device according to a fifth example embodiment of this invention.

FIG. 25 is a block diagram for illustrating a configuration of a drowsiness estimating device 100D according to a fifth example embodiment of this invention. The illustrated drowsiness estimating device 100D may be implemented by a computer which operates under program control.

The illustrated drowsiness estimating device 100D is similar in structure and operation to the drowsiness estimating device 100 illustrated in FIG. 1 except that the feature calculator is different in structure as will later be described. The feature calculator is therefore depicted by the reference numeral 160D. The same reference numerals are assigned to parts similar in function to those illustrated in FIG. 1, and description thereof will be omitted in order to simplify the description.

Figure 26:
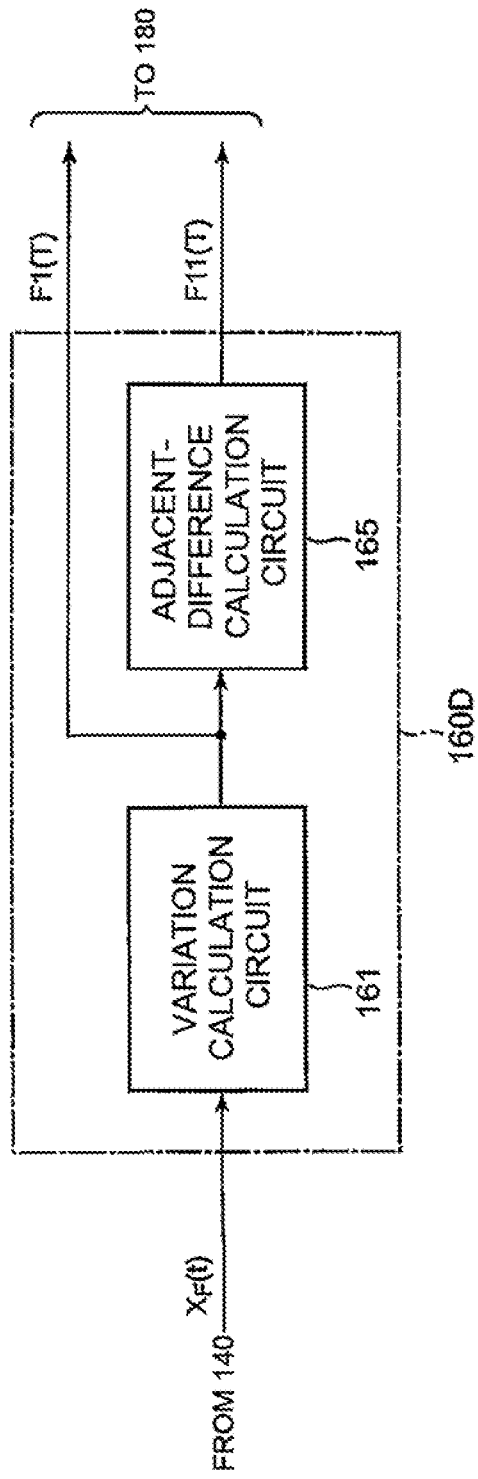
FIG. 26 is a block diagram for illustrating a configuration of a feature calculator for use in the drowsiness estimating device according to the fifth example embodiment illustrated in FIG. 25.

FIG. 26 is a block diagram for illustrating a configuration of the feature calculator 160D. The illustrated feature calculator 160D is similar in structure and operation to the feature calculator 160 illustrated in FIG. 13 except that an adjacent-difference calculation circuit 165 is further provided. Accordingly, the feature calculator 160D comprises the variation calculation circuit 161 and the adjacent-difference calculation circuit 165.

The adjacent-difference calculation circuit 165 calculates an absolute value of a difference between the first feature F1(T) calculated in one feature calculation window width $(T_M)$ [sec] and the first feature F1(T−1) calculated in another feature calculation window width $(T_M)$ [sec] adjacent thereto (that will be called "a difference between adjacent windows" hereinafter), and produces the difference between adjacent windows as a fifth feature F11(T). Accordingly, the adjacent-difference calculation circuit 165 serves as a fifth feature calculation circuit for calculating and producing, as the fifth feature F11(T), the difference between adjacent windows in the first feature F1(T). The difference between adjacent windows has a large value in the drowsy state and has a small value in the wide-awake state, and is therefore useful in drowsiness estimation.

The difference between adjacent windows, namely, the fifth feature F11(T) is represented by the following Math. 12:

$$F11(T)=|F1(T)-F(T-1)| \qquad \text{[Math. 12]}$$

Although the difference F11(T) between adjacent windows in the first feature F1(T) is used as the fifth feature in the fifth example embodiment, the present invention is not limited thereto. For instance, as the fifth feature, a difference F21(T) between adjacent windows in the above-mentioned second feature F2(T), a difference F31(T) between adjacent windows in the above-mentioned third feature F3(T), or a difference F41(T) between adjacent windows in the above-mentioned fourth feature F4(T) may be used.

[Description of Operation]

Figure 27:
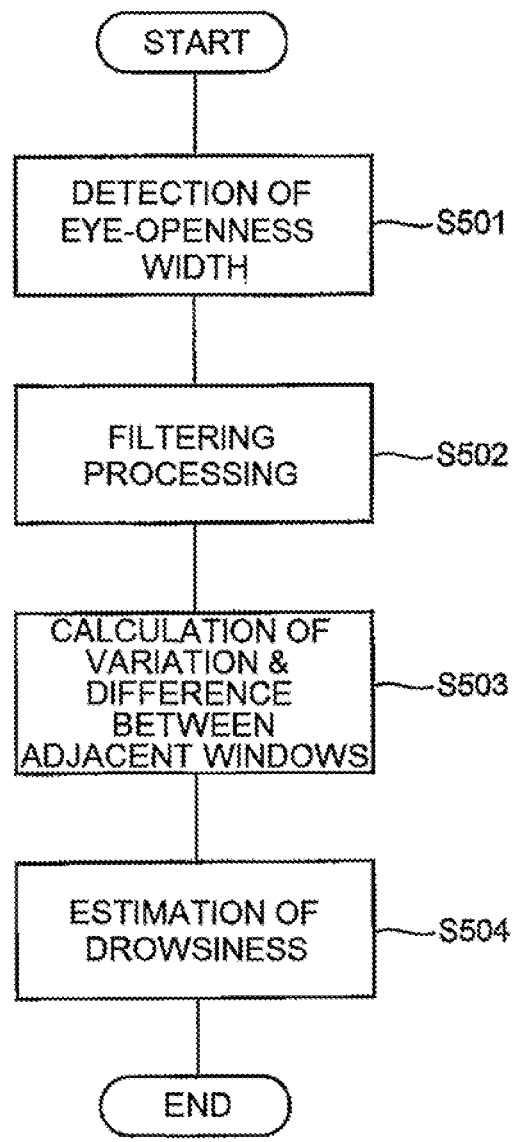
FIG. 27 is a flow chart for use in describing an operation of the drowsiness estimating device according to the fifth example embodiment illustrated in FIG. 25.

Next, referring to a flow chart of FIG. 27, description will proceed to an operation of the drowsiness estimating device 100D according to the fifth example embodiment.

First, the eye-openness width detector 120 detects the eye-openness width from the moving image signal V(t) to produce the time-series signal X(t) of the eye-openness width (Step S501).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S502).

Subsequently, the feature calculator 160D calculates the variation in the filtered time-series signal $X_F(t)$ of the eye-openness width within the feature calculation window width $T_M$ [sec] to produce the variation as the first feature F(T), and calculates the difference in first feature F1(T) between the two adjacent feature calculation window widths $T_M$ [sec] (difference between adjacent windows) to produce the difference between adjacent windows as the fifth feature F11(T) (Step S503).

Finally, the drowsiness estimator 180 estimates the drowsiness evaluated value of the subject 20 from the first feature F1(T) and the fifth feature F11(T) to produce the estimated result ER (Step S504).

Although both of the first feature F1(T) and the fifth feature F11(T) are used as features supplied to the drowsiness estimator 180 in the fifth example embodiment, the present invention is not limited thereto. That is, only the fifth feature F11(T) may be used as a feature supplied to the drowsiness estimator 180. In this event, the drowsiness estimator 180 estimates the drowsiness evaluated value of the subject 20 from the fifth feature F1(T) to produce the estimated result ER.

[Description of Effect]

Next, an effect of the fifth example embodiment will be described.

According to the fifth example embodiment of the present invention, it is possible to estimate the drowsiness with equivalent or more accuracy as compared with the first example embodiment. This is because information usable in drowsiness estimation increases by adding, as the fifth feature, the difference between adjacent windows. By simply and appropriately capturing a change for a longer time interval, accuracy of the drowsiness estimation is improved because the difference between adjacent windows becomes large in the drowsy state.

Each part of the drowsiness estimating device 100D may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned fifth example embodiment with a different expression, it is possible to implement the example embodiment by making a computer to be operated as the drowsiness estimating device 100D act as the eye-openness width detector 120, the filtering circuitry 140, the feature calculator 160D, and the drowsiness estimator 180 according to the drowsiness estimating program developed in the RAM.

Sixth Example Embodiment

Figure 28:
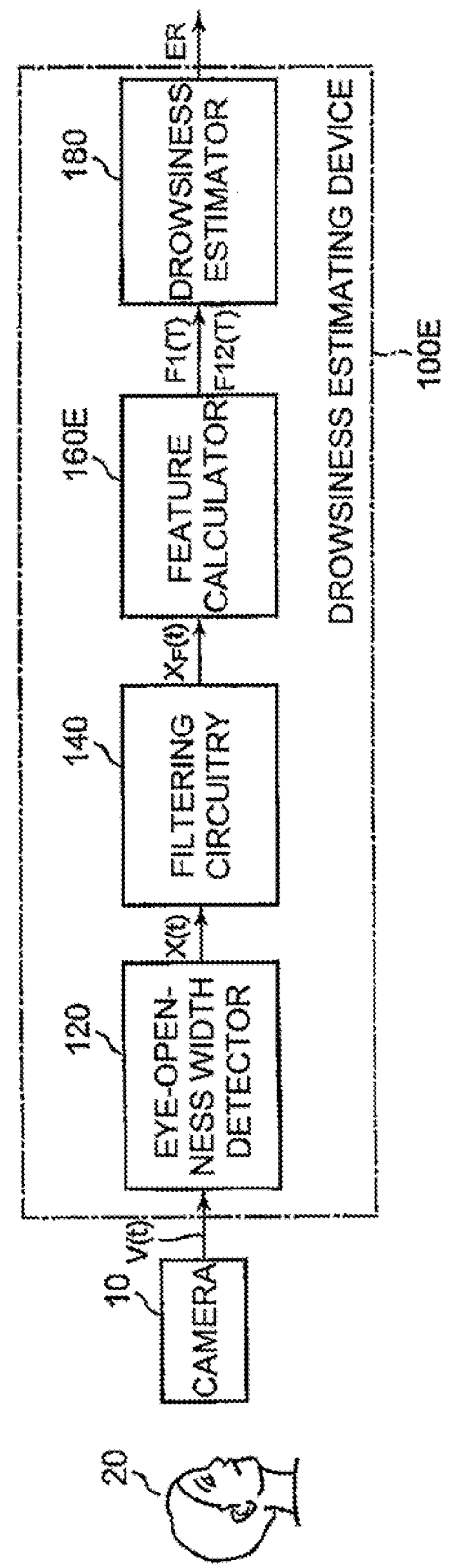
FIG. 28 is a block diagram for illustrating a configuration of a drowsiness estimating device according to a sixth example embodiment of this invention.

FIG. 28 is a block diagram for illustrating a configuration of a drowsiness estimating device 100E according to a sixth example embodiment of this invention. The illustrated drowsiness estimating device 100E may be implemented by a computer which operates under program control.

The illustrated drowsiness estimating device 100E is similar in structure and operation to the drowsiness estimating device 100 illustrated in FIG. 1 except that the feature calculator is different in structure as will later be described. The feature calculator is therefore depicted by the reference numeral 160E. The same reference numerals are assigned to parts similar in function to those illustrated in FIG. 1, and description thereof will be omitted in order to simplify the description.

Figure 29:
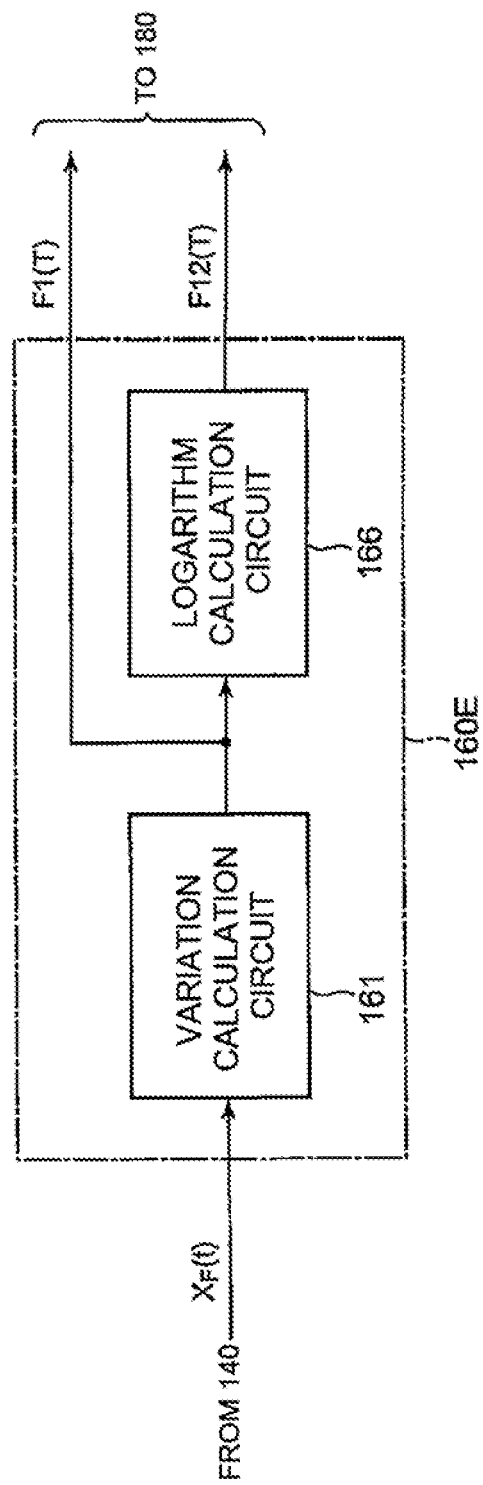
FIG. 29 is a block diagram for illustrating a configuration of a feature calculator for use in the drowsiness estimating device according to the sixth example embodiment illustrated in FIG. 28.

FIG. 29 is a block diagram for illustrating a configuration of the feature calculator 160E. The illustrated feature calculator 160E is similar in structure and operation to the feature calculator 160 illustrated in FIG. 13 except that a logarithm calculation circuit 166 is further provided. Accordingly, the feature calculator 160E comprises the variation calculation circuit 161 and the logarithm calculation circuit 166.

The logarithm calculation circuit 166 calculates a logarithm of the first feature F1(T) and produces the logarithm as a sixth feature F12(T). Accordingly, the logarithm calculation circuit 166 serves as a sixth feature calculation circuit for calculating and producing the logarithm of the first feature F1(T) as the sixth feature F12(T). The drowsiness evaluated values of a target of estimation is calculated by a human being. It is generally said that senses of the human being follow the logarithm, and the drowsiness evaluated values also follow the logarithm. Therefore, by calculating the logarithm of the feature, it is possible to linearize a relationship between the feature and the drowsiness evaluated values.

The logarithm of the first feature, namely, the sixth feature F12(T) is represented by the following Math. 13:

$$F12(T)=\text{Log}\{F1(T)+\alpha\}, \quad [\text{Math. 13}]$$

where α represent a small value, for example, $10^{-6}$. The small value α is added to the first feature F1(T) in order to prevent a content of the logarithm from becoming zero.

Although the logarithm of the first feature F1(T) is used as the sixth feature in the sixth example embodiment, the present invention is not limited thereto. For instance, as the sixth feature, a logarithm F22(T) of the above-mentioned second feature F2(T), a logarithm F32(T) of the above-mentioned third feature F3(T), a logarithm F42(T) of the above-mentioned fourth feature F4(T), or a logarithm F112(T) of the above-mentioned fifth feature F11(T) may be used.

[Description of Operation]

Figure 30:
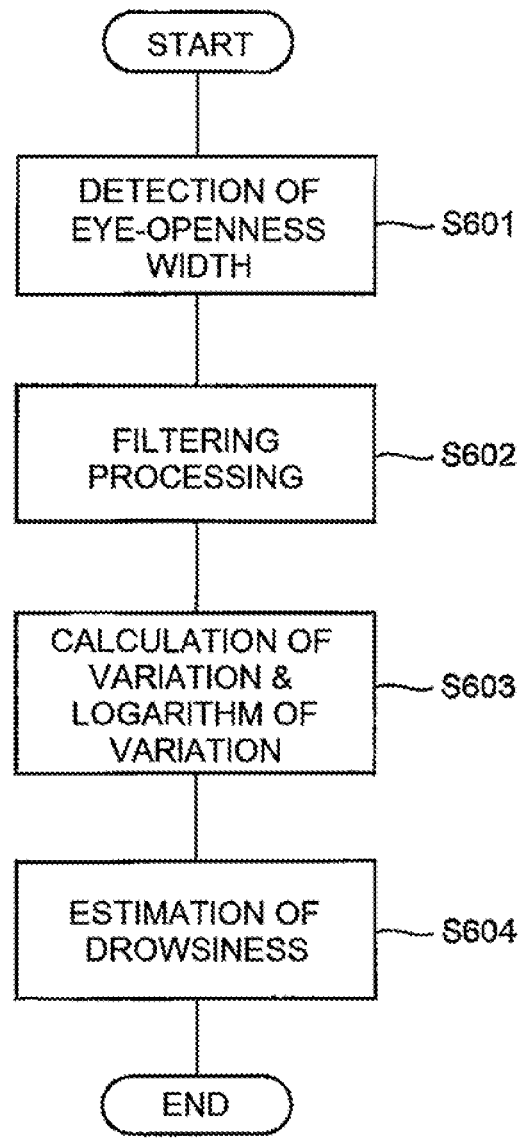
FIG. 30 is a flow chart for use in describing an operation of the drowsiness estimating device according to the sixth example embodiment illustrated in FIG. 28.

Next, referring to a flow chart of FIG. 30, description will proceed to an operation of the drowsiness estimating device 100E according to the sixth example embodiment.

First, the eye-openness width detector 120 detects the eye-openness width from the moving image signal V(t) to produce the time-series signal X(t) of the eye-openness width (Step S601).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S602).

Subsequently, the feature calculator 160E calculates the variation in the filtered time-series signal $X_F(t)$ of the eye-openness width within the feature calculation window width $T_M$ [sec] to produce the variation as the first feature F1(T), and calculates the logarithm of the variation to produce the logarithm as the sixth feature F12(T) (Step S603).

Finally, the drowsiness estimator 180 estimates the drowsiness evaluated value of the subject 20 from the first feature F1(T) and the sixth feature F12(T) to produce the estimated result ER (Step S604).

Although both of the first feature F1(T) and the sixth feature F12(T) are used as features supplied to the drowsiness estimator 180 in the sixth example embodiment, the present invention is not limited thereto. That is, only the sixth feature F12(T) may be used as a feature supplied to the drowsiness estimator 180. In this event, the drowsiness estimator 180 estimates the drowsiness evaluated value of the subject 20 from the sixth feature F12(T) to produce the estimated result ER.

[Description of Effect]

Next, an effect of the sixth example embodiment will be described.

According to the sixth example embodiment of the present invention, it is possible to estimate the drowsiness with equivalent or more accuracy as compared with the first example embodiment. This is because the relationship between the feature and the drowsiness evaluated values becomes linear by using the logarithm of the first feature as the sixth feature. Since the relationship becomes simple, the relationship is easily estimated and accuracy of the drowsiness estimation is improved.

Each part of the drowsiness estimating device 100E may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned sixth example embodiment with a different expression, it is possible to implement the example embodiment by making a computer to be operated as the drowsiness estimating device 100E act as the eye-openness width detector 120, the filtering circuitry 140, the feature calculator 160E, and the drowsiness estimator 180 according to the drowsiness estimating program developed in the RAM.

Seventh Example Embodiment

Figure 31:
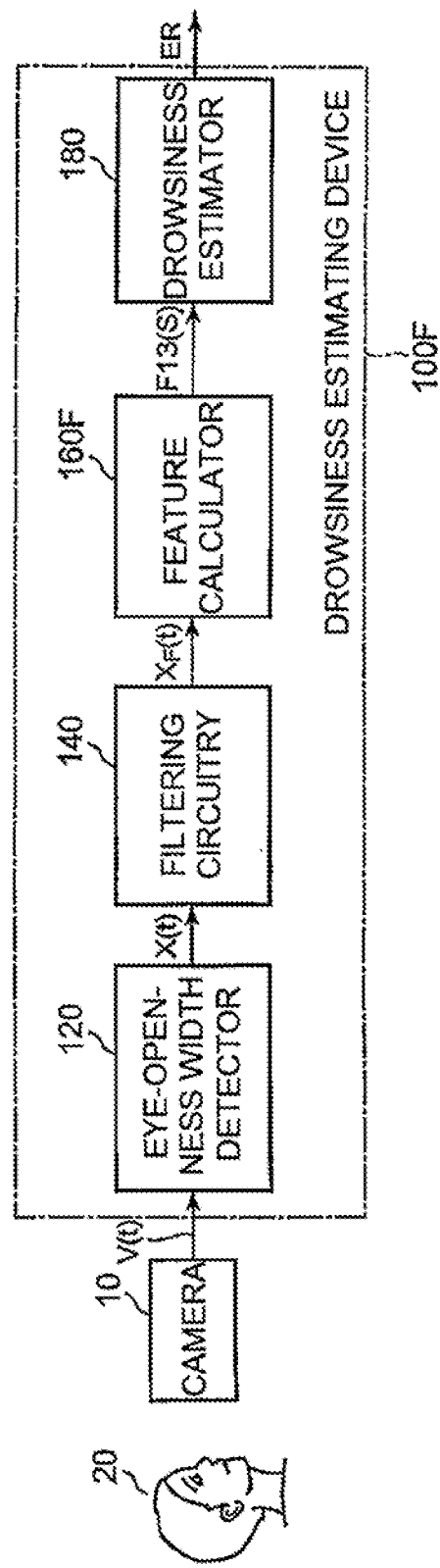
FIG. 31 is a block diagram for illustrating a configuration of a drowsiness estimating device according to a seventh example embodiment of this invention.

FIG. 31 is a block diagram for illustrating a configuration of a drowsiness estimating device 100F according to a seventh example embodiment of this invention. The illustrated drowsiness estimating device 100F may be implemented by a computer which operates under program control.

The illustrated drowsiness estimating device 100F is similar in structure and operation to the drowsiness estimating device 100 illustrated in FIG. 1 except that the feature calculator is different in structure as will later be described. The feature calculator is therefore depicted by the reference numeral 160F. The same reference numerals are assigned to parts similar in function to those illustrated in FIG. 1, and description thereof will be omitted in order to simplify the description.

Figure 32:
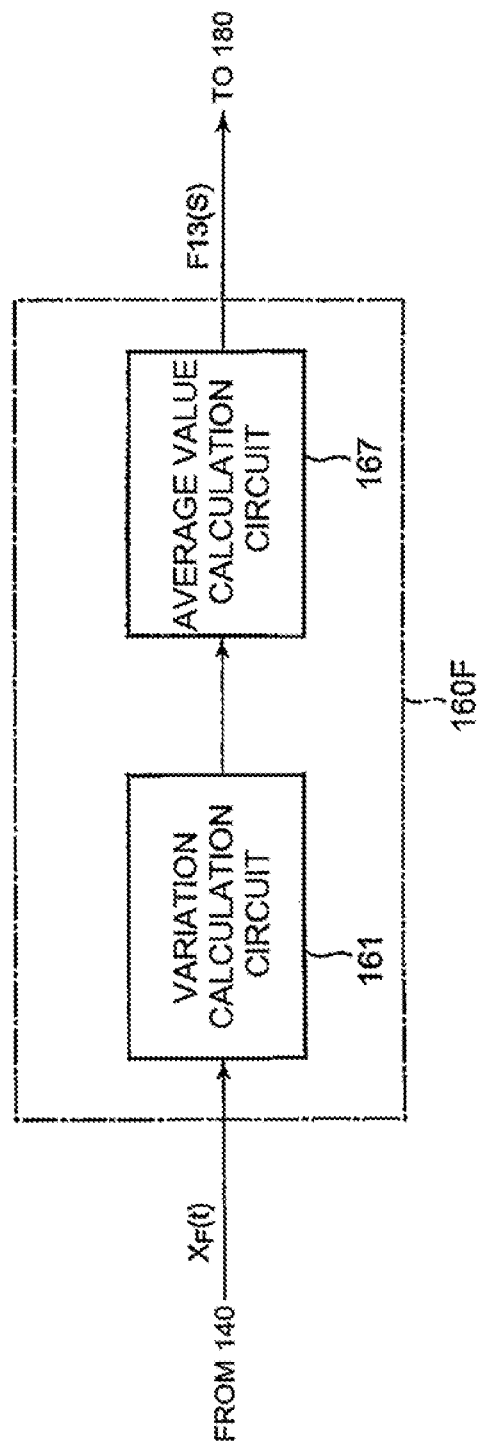
FIG. 32 is a block diagram for illustrating a configuration of a feature calculator for use in the drowsiness estimating device according to the seventh example embodiment illustrated in FIG. 31.

FIG. 32 is a block diagram for illustrating a configuration of the feature calculator 160F. The illustrated feature calculator 160F uses, as a feature, a statistic of any of the above-mentioned features. The illustrated feature calculator 160F is characterized by calculating, per statistic calculation window width $T_K$ [sec], a statistic F(S) of any one of the above-mentioned features, as will later be described, and using the statistic as the feature. Herein, S is an index of time and represents a window number (0, 1, 2, . . . ) of a statistic calculation window. In the example being illustrated, it is assumed that the number of the features within the statistic calculation window width $T_K$ [sec] is equal to K. In the example illustrated in FIG. 4, the statistic calculation window width $T_K$ is equal to 60[sec] and accordingly the number K of the features is equal to six.

In the example being illustrated, the first feature F1(T) is used as the above-mentioned feature whereas an average value of the first feature F1(T) is used as the statistic. Accordingly, the feature calculator 160F is similar in structure and operation to the feature calculator 160 illustrated in FIG. 13 except that an average value calculation circuit 167 is further provided. The average value calculation circuit 167 serves as a statistic calculation circuit.

The average value calculation circuit 167 calculates an average value of the first feature F1(T) within the statistic calculation window width $T_K$ [sec] and produces the average value as a seventh feature F13(S). Accordingly, the average value calculation circuit 167 serves as a seventh feature calculation circuit for calculating and producing, as the seventh feature F13(S), the average value of the first feature F1(T) per statistic calculation window width $T_K$ [sec].

The average value of the first feature, namely, the seventh feature F13(S) is represented by the following Math. 14. Herein, average [ ] is an operator for calculating an average value of elements:

$$F13(S)=\text{average}[F1(S*K+T), \ldots, F1(S*K+T-K+1)] \quad \text{[Math. 14]}$$

Although the average value of the first feature F1(T) is used as the seventh feature (statistic) in the seventh example embodiment, the present invention is not limited thereto. For instance, as the seventh feature, an average value F23(S) of the above-mentioned second feature F2(T), an average value F33(S) of the above-mentioned third feature F3(T), an average value F43(S) of the above-mentioned fourth feature F4(T), an average value F13(S) of the above-mentioned fifth feature F1(T), or an average value F123(S) of the above-mentioned sixth feature F12(T) may be used.

[Description of Operation]

Figure 33:
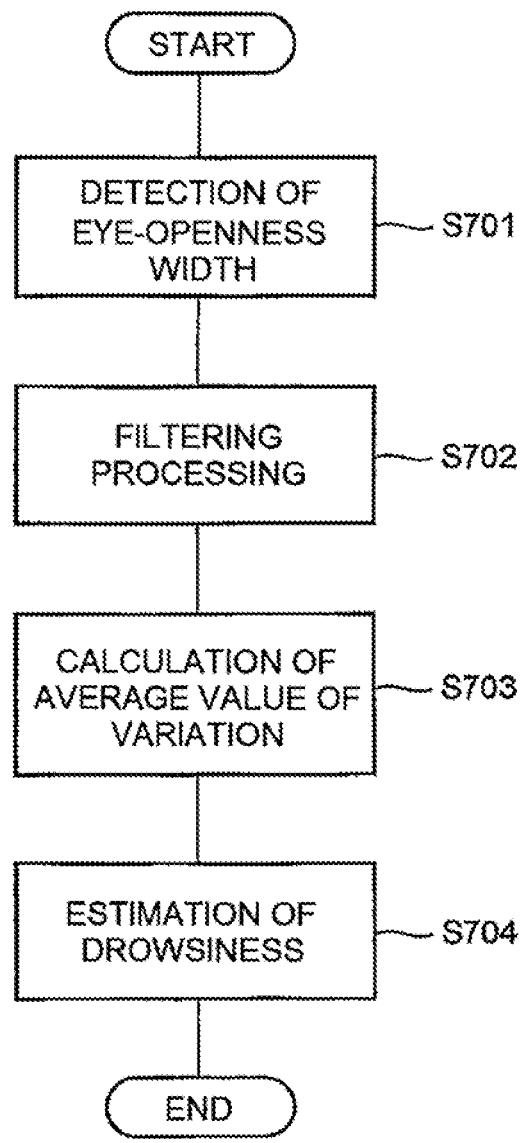
FIG. 33 is a flow chart for use in describing an operation of the drowsiness estimating device according to the seventh example embodiment illustrated in FIG. 31.

Next, referring to a flow chart of FIG. 33, description will proceed to an operation of the drowsiness estimating device 100F according to the seventh example embodiment.

First, the eye-openness width detector 120 detects the eye-openness width from the moving image signal V(t) to produce the time-series signal X(t) of the eye-openness width (Step S701).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S702).

Subsequently, the feature calculator 160F calculates the variation in the filtered time-series signal $X_F(t)$ of the eye-openness width within the feature calculation window width $T_M$ [sec], calculates the average value of the variation within the statistic calculation window width $T_K$ [sec], and produces the average value as the seventh feature F13(S) (Step S703).

Finally, the drowsiness estimator 180 estimates the drowsiness evaluated value of the subject 20 from the seventh feature F13(S) to produce the estimated result ER (Step S704).

In the seventh example embodiment, the seventh feature F13(S) is used as the feature supplied to the drowsiness estimator 180. In this event, the drowsiness estimator 180 estimates the drowsiness evaluated value of the subject 20 from the seventh feature F13(S) to produce the estimated result ER.

[Description of Effect]

Next, an effect of the seventh example embodiment will be described.

According to the seventh example embodiment of the present invention, it is possible to estimate the drowsiness more stably as compared with the first example embodiment. This is because a stable characteristic for a longer time interval is obtained by using the statistic (average value) of the first feature as the seventh feature.

Each part of the drowsiness estimating device 100F may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned seventh example embodiment with a different expression, it is possible to implement the example embodiment by making a computer to be operated as the drowsiness estimating device 100F act as the eye-openness width detector 120, the filtering circuitry 140, the feature calculator 160F, and the drowsiness estimator 180 according to the drowsiness estimating program developed in the RAM.

Eighth Example Embodiment

Figure 34:
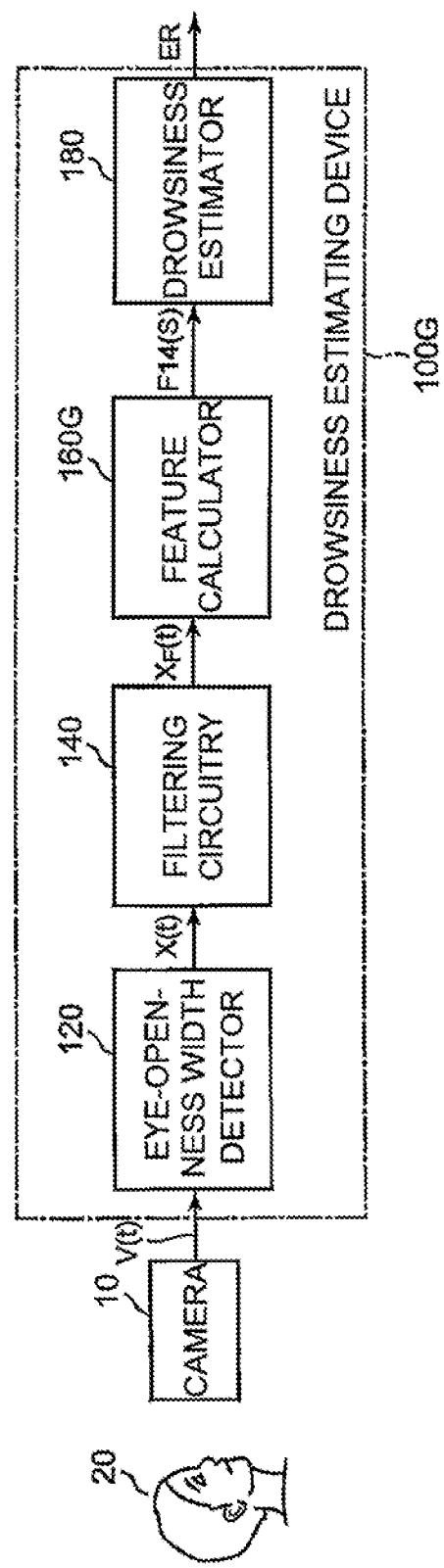
FIG. 34 is a block diagram for illustrating a configuration of a drowsiness estimating device according to an eighth example embodiment of this invention.

FIG. 34 is a block diagram for illustrating a configuration of a drowsiness estimating device 100G according to an eighth example embodiment of this invention. The illustrated drowsiness estimating device 100G may be implemented by a computer which operates under program control.

The illustrated drowsiness estimating device 100G is similar in structure and operation to the drowsiness estimating device 100 illustrated in FIG. 1 except that the feature calculator is different in structure as will later be described. The feature calculator is therefore depicted by the reference numeral 160G. The same reference numerals are assigned to parts similar in function to those illustrated in FIG. 1, and description thereof will be omitted in order to simplify the description.

Figure 35:
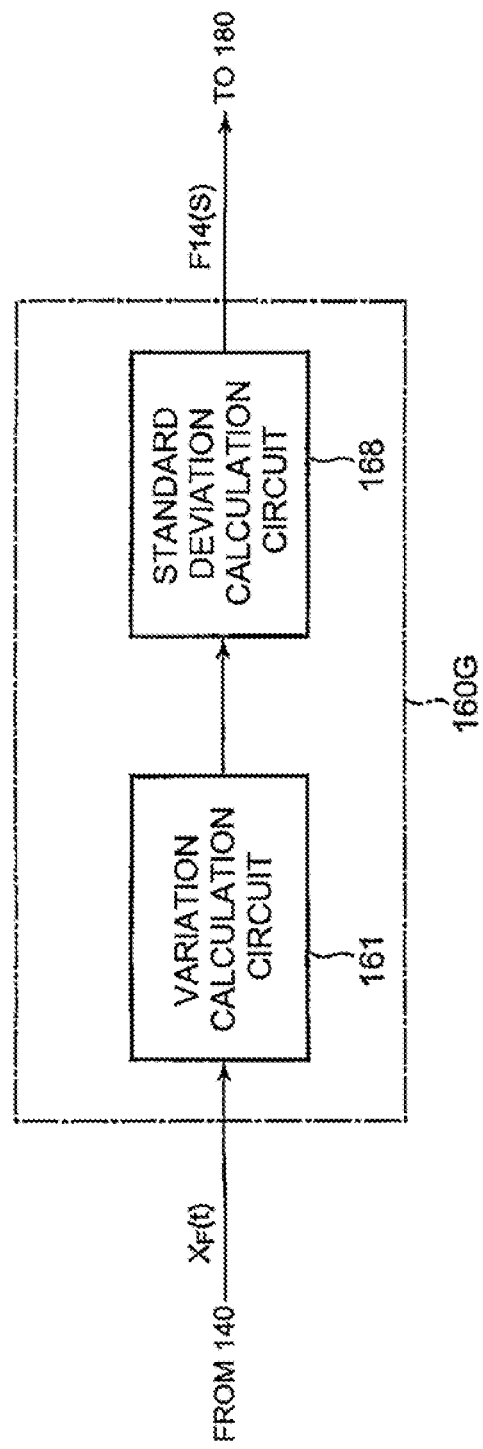
FIG. 35 is a block diagram for illustrating a configuration of a feature calculator for use in the drowsiness estimating device according to the eighth example embodiment illustrated in FIG. 34.

FIG. 35 is a block diagram for illustrating a configuration of the feature calculator 160G. The illustrated feature calculator 160G uses, as the above-mentioned statistic, a standard deviation of the first feature F1(T). That is, the feature calculator 160G is similar in structure and operation to the feature calculator 160F illustrated in FIG. 32 except that a standard deviation calculation circuit 168 is provided instead of the average value calculation circuit 167. The standard deviation calculation circuit 168 also serves as the statistic calculation circuit.

The standard deviation calculation circuit 168 calculates a standard deviation of the first feature F1(T) within the statistic calculation window width $T_K$ [sec] and produces the standard deviation as an eighth feature F14(S). Accordingly, the standard deviation calculation circuit 168 serves as an eighth feature calculation circuit for calculating and producing, as the eighth feature F14(S), the standard deviation of the first feature F1(T) per statistic calculation window width $T_K$ [sec].

The standard deviation of the first feature, namely, the eighth feature F14(S) is represented by the following Math. 15. Herein, standard_dev [ ] is an operator for calculating a standard deviation of elements:

$$F14(S)=\text{standard\_dev}[F1(S*K+T), \ldots, F1(S*K+T-K+1)] \quad \text{[Math. 15]}$$

Although the standard deviation of the first feature F1(T) is used as the eighth feature (statistic) in the eighth example embodiment, the present invention is not limited thereto. For instance, as the eighth feature, a standard deviation F24(S) of the above-mentioned second feature F2(T), a standard deviation F34(S) of the above-mentioned third feature F3(T), a standard deviation F44(S) of the above-mentioned fourth feature F4(T), a standard deviation F114(S) of the above-mentioned fifth feature F11(T), or a standard deviation F124(S) of the above-mentioned sixth feature F12(T) may be used.

[Description of Operation]

Figure 36:
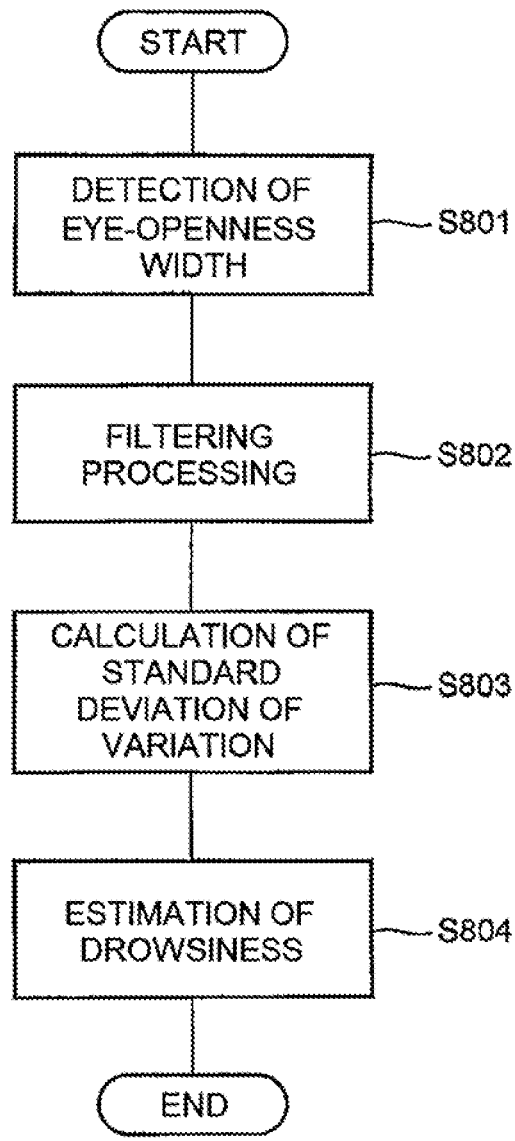
FIG. 36 is a flow chart for use in describing an operation of the drowsiness estimating device according to the eighth example embodiment illustrated in FIG. 34.

Next, referring to a flow chart of FIG. 36, description will proceed to an operation of the drowsiness estimating device 100G according to the eighth example embodiment.

First, the eye-openness width detector 120 detects the eye-openness width from the moving image signal V(t) to produce the time-series signal X(t) of the eye-openness width (Step S801).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S82).

Subsequently, the feature calculator 160G calculates the variation in the filtered time-series signal $X_F(t)$ of the eye-openness width within the feature calculation window width $T_M$ [sec], calculates the standard deviation of the variation within the statistic calculation window width $T_K$ [sec], and produces the standard deviation as the eighth feature F14(S) (Step S803).

Finally, the drowsiness estimator 180 estimates the drowsiness evaluated value of the subject 20 from the eighth feature F14(S) to produce the estimated result ER (Step S804).

In the eighth example embodiment, the eighth feature F14(S) is used as the feature supplied to the drowsiness estimator 180. In this event, the drowsiness estimator 180 estimates the drowsiness evaluated value of the subject 20 from the eighth feature F14(S) to produce the estimated result ER.

[Description of Effect]

Next, an effect of the eighth example embodiment will be described.

According to the eighth example embodiment of the present invention, it is possible to estimate the drowsiness more stably as compared with the first example embodiment. This is because a stable characteristic for a longer time interval is obtained by using the statistic (standard deviation) of the first feature as the eighth feature.

Each part of the drowsiness estimating device 1000 may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned eighth example embodiment with a different expression, it is possible to implement the example embodiment by making a computer to be operated as the drowsiness estimating device 100G act as the eye-openness width detector 120, the filtering circuitry 140, the feature calculator 160G, and the drowsiness estimator 1g0 according to the drowsiness estimating program developed in the RAM.

Ninth Example Embodiment

Figure 37:
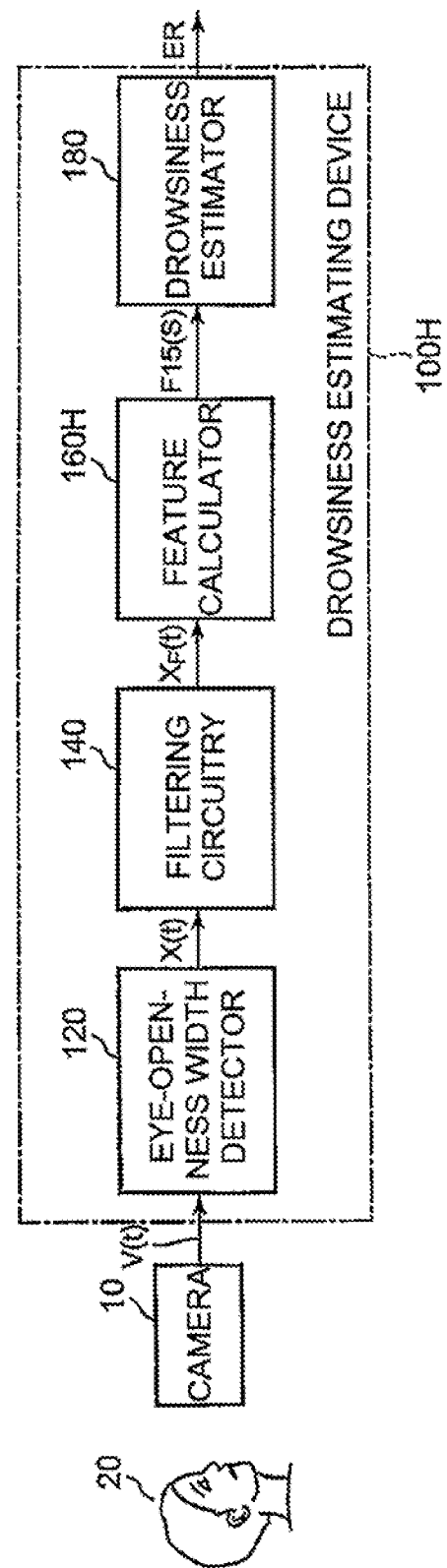
FIG. 37 is a block diagram for illustrating a configuration of a drowsiness estimating device according to a ninth example embodiment of this invention.

FIG. 37 is a block diagram for illustrating a configuration of a drowsiness estimating device 100H according to a ninth example embodiment of this invention. The illustrated drowsiness estimating device 100H may be implemented by a computer which operates under program control.

The illustrated drowsiness estimating device 100H is similar in structure and operation to the drowsiness estimating device 100 illustrated in FIG. 1 except that the feature calculator is different in structure as will later be described. The feature calculator is therefore depicted by the reference numeral 160H. The same reference numerals are assigned to parts similar in function to those illustrated in FIG. 1, and description thereof will be omitted in order to simplify the description.

Figure 38:
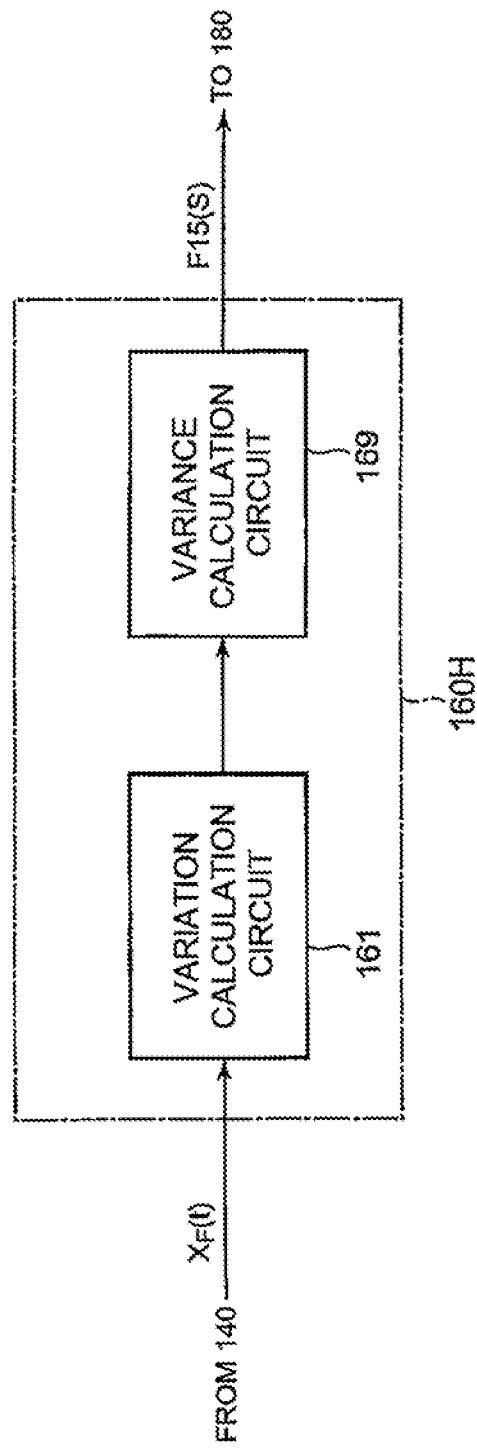
FIG. 38 is a block diagram for illustrating a configuration of a feature calculator for use in the drowsiness estimating device according to the ninth example embodiment illustrated in FIG. 37.

FIG. 38 is a block diagram for illustrating a configuration of the feature calculator 160H. The illustrated feature calculator 160H uses, as the above-mentioned statistic, a variance of the first feature F1(T). That is, the feature calculator 160H is similar in structure and operation to the feature calculator 160F illustrated in FIG. 32 except that a variance calculation circuit 169 is provided instead of the average value calculation circuit 167. The variance calculation circuit 169 also serves as the statistic calculation circuit.

The variance calculation circuit 169 calculates a variance of the first feature F1(T) within the statistic calculation window width $T_K$ [sec] and produces the variance as a ninth feature F15(S). Accordingly, the variance calculation circuit 169 serves as a ninth feature calculation circuit for calculating and producing, as the ninth feature F15(S), the variance of the first feature F1(T) per statistic calculation window width $T_K$ [sec].

The variance of the first feature, namely, the ninth feature F15(S) is represented by the following Math. 16. Herein, variance [ ] is an operator for calculating a variance of elements:

$$F15(S)=\text{variance}[F1(S*K+T), \ldots, F1(S*K+T-K+1)] \quad \text{[Math. 16]}$$

Although the variance of the first feature F1(T) is used as the ninth feature (statistic) in the ninth example embodiment, the present invention is not limited thereto. For instance, as the ninth feature, a variance F25(S) of the above-mentioned second feature F2(T), a variance F35(S) of the above-mentioned third feature 3(T), a variance F45(S) of the above-mentioned fourth feature F4(T), a variance F115 (S) of the above-mentioned fifth feature F11(T), or a variance F125(S) of the above-mentioned sixth feature F12(T) may be used.

[Description of Operation]

Figure 39:
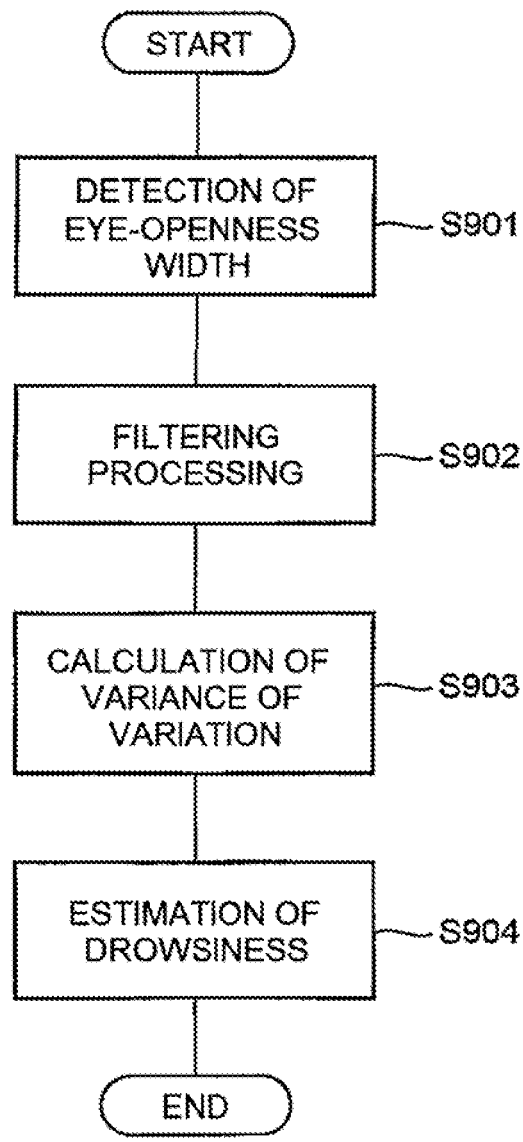
FIG. 39 is a flow chart for use in describing an operation of the drowsiness estimating device according to the ninth example embodiment illustrated in FIG. 37.

Next, referring to a flow chart of FIG. 39, description will proceed to an operation of the drowsiness estimating device 100H according to the ninth example embodiment.

First, the eye-openness width detector 120 detects the eye-openness width from the moving image signal V(t) to produce the time-series signal X(t) of the eye-openness width (Step S901).

Next, the filtering circuitry 140 filters the time-series signal X(t) of the eye-openness width so as to eliminate signal changes due to blinking of the subject 20 therefrom to produce the filtered time-series signal $X_F(t)$ of the eye-openness width (Step S902).

Subsequently, the feature calculator 160H calculates the variation in the filtered time-series signal $X_F(t)$ of the eye-openness width within the feature calculation window width $T_M$ [sec], calculates the variance of the variation within the statistic calculation window width $T_K$ [sec], and produces the variance as the ninth feature F5(S)(Step S903).

Finally, the drowsiness estimator 180 estimates the drowsiness evaluated value of the subject 20 from the ninth feature F15(S) to produce the estimated result ER (Step S904).

In the ninth example embodiment, the ninth feature F15 (S) is used as the feature supplied to the drowsiness estimator 180. In this event, the drowsiness estimator 180 estimates the drowsiness evaluated value of the subject 20 from the ninth feature F15(S) to produce the estimated result ER.

[Description of Effect]

Next, an effect of the ninth example embodiment will be described.

According to the ninth example embodiment of the present invention, it is possible to estimate the drowsiness more stably as compared with the first example embodiment. This is because a stable characteristic for a longer time interval is obtained by using the statistic (variance) of the first feature as the ninth feature.

Each part of the drowsiness estimating device 100H may be implemented by a combination of hardware and software. In a form in which the hardware and the software are combined, the respective parts are implemented as various kinds of means by developing a drowsiness estimating program in the RAM (random access memory) and making hardware such as the control unit (CPU (central processing unit)) operate based on the drowsiness estimating program. The drowsiness estimating program may be recorded in a recording medium to be distributed. The drowsiness estimating program recorded in the recording medium is read into a memory via a wire, wirelessly, or via the recording medium itself to operate the control unit and so on. By way of example, the recoding medium may be an optical disc, a magnetic disk, a semiconductor memory device, a hard disk, or the like.

Explaining the above-mentioned ninth example embodiment with a different expression, it is possible to implement the example embodiment by making a computer to be operated as the drowsiness estimating device 100H act as the eye-openness width detector 120, the filtering circuitry 140, the feature calculator 160H, and the drowsiness estimator 180 according to the drowsiness estimating program developed in the RAM.

Specific configurations of the present invention are not limited to the above-mentioned example embodiments, and the present invention includes changes in the scope without departing from the gist of the present invention.

While the invention has been particularly shown and described with reference to example embodiments (examples) thereof, the invention is not limited these example embodiments (examples). It will be understood by those of ordinary skill in the art that various changes in form and details may be made therein within the scope of the present invention.

The whole or part of the example embodiments described above may be described as, but not limited to, the following supplementary notes.

(Supplementary Note 1)

A drowsiness estimating device for estimating, from a time-series signal of an eye-openness width of a subject, drowsiness of the subject, the drowsiness estimating device comprising:

a filtering circuitry configured to filter the time-series signal of the eye-openness width so as to eliminate signal changes due to blinking of the subject therefrom to produce a filtered time-series signal of the eye-openness width;

a feature calculator configured to calculate a feature from at least the filtered time-series signal of the eye-openness width; and a drowsiness estimator configured to estimate a drowsiness evaluated value from the feature to produce an estimated result, wherein the feature calculator at least includes a first feature calculation circuit configured to calculate a variation in the filtered time-series signal of the eye-openness width within a feature calculation window width ($T_M$) [sec] to produce the variation as a first feature.

(Supplementary Note 2)

The drowsiness estimating device according to Supplementary Note 1, wherein the time-series signal of the eye-openness width is a time-series signal of fs [frames/sec], wherein a relationship of $N=T_N \times fs$ holds, where N represents the number of frames and $T_N$ [sec] represents a filtering calculation window width, wherein the filtering circuitry is configured to filter the time-series signal of the eye-openness width per the filtering calculation window width ($T_N$) to substitute the time-series signal with a predetermined value, and to produce a substituted signal as the filtered time-series signal of the eye-openness width.

(Supplementary Note 3)

The drowsiness estimating device according to Supplementary Note 2, wherein the filtering calculation window width ($T_N$) is not less than 0.1 [sec], wherein the filtering circuitry comprises a maximum value acquisition circuit configured to acquire, as the predetermined value, a maximum value of the time-series signal of the eye-openness width within the filtering calculation window width ($T_N$).

(Supplementary Note 4)

The drowsiness estimating device according to Supplementary Note 2, wherein P is an integer which is not less than two and the filtering calculation window width (T) is not less than 0.2 [sec], wherein the filtering circuitry comprises a percentile calculation circuit configured to calculate, as the predetermined value, a value of a (P−1)P-th percentile of the time-series signal of the eye-openness width within the filtering calculation window width ($T_N$) or an average value of the (P−1)P-th percentile and greater values.

(Supplementary Note 5)

The drowsiness estimating device according to Supplementary Note 2, wherein the filtering calculation window width ($T_N$) is not less than 1 [sec], wherein the filtering circuitry comprises an average value calculation circuit configured to calculate, as the predetermined value, an average value of the time-series signal of the eye-openness width within the filtering calculation window width ($T_N$).

(Supplementary Note 6)

The drowsiness estimating device according to Supplementary Note 1, wherein the time-series signal of the eye-openness width is a time-series signal of fs [frames/sec], wherein the filtering circuitry comprises a low-pass filter having a cut-off frequency fc [Hz] which is sufficiently lower than the above-mentioned fs and is lower than 6 Hz.

(Supplementary Note 7)

The drowsiness estimating device according to any one of Supplementary Notes 1 to 6, wherein the feature calculator further comprises a second feature calculation circuit configured to calculate inter-frame differences of the time-series signal of the eye-openness width, to calculate a maximum value of the inter-frame differences within the feature calculation window width ($T_M$) [sec], and to produce the maximum value as a second feature.

(Supplementary Note 8)

The drowsiness estimating device according to any one of Supplementary Notes 1 to 7, wherein the feature calculator further comprises a third feature calculation circuit configured to detect eye closure from the time-series signal of the eye-openness width, to calculate an eye-closure ratio within the first predetermined time window width ($T_M$) [sec], and to produce the eye-closure ratio as a third feature.

(Supplementary Note 9)

The drowsiness estimating device according to any one of Supplementary Notes 1 to 8, wherein the feature calculator further comprises a fourth feature calculation circuit configured to calculate motion differences of the eye-openness width between a left eye and a right eye from the time-series signal of the eye-openness width, to calculate an average value of the motion differences within the feature calculation window width ($T_M$) [sec], and to produce the average value of the motion differences as a fourth feature.

(Supplementary Note 10)

The drowsiness estimating device according to Supplementary Note 9, wherein the feature calculator further comprises a fifth feature calculation circuit configured to calculate differences between respective two adjacent values of the first through the fourth features, which are calculated by the first through the fourth feature calculation circuits in two adjacent feature calculation window widths ($T_M$) [sec], respectively, to produce a selected one of the differences as a fifth feature.

(Supplementary Note 11)

The drowsiness estimating device according to Supplementary Note 10, wherein the feature calculator further comprises a sixth feature calculation circuit configured to calculate logarithms of the first through the fifth features, which are calculated by the first through the fifth feature calculation circuits, respectively, to produce a selected one of the logarithms as a sixth feature.

(Supplementary Note 12)

The drowsiness estimating device according to Supplementary Note 11, wherein the feature calculator further comprises a statistic calculation circuit configured to calculate, within a statistic calculation window width ($T_K$) [sec] which is a multiple of the feature calculation window width ($T_M$) [sec], a statistic of a selected one of the first through the sixth features, which are calculated by the first through the sixth feature calculation circuits, respectively, per the feature calculation window width ($T_M$) [sec].

(Supplementary Note 13)

The drowsiness estimating device according to Supplementary Note 12, wherein the statistic calculation circuit is configured to calculate, as the statistic, at least one selected from an average value, a standard deviation, and a variance of a selected one of the first through the sixth features per the statistic calculation window width ($T_M$) [sec].

(Supplementary Note 14)

A drowsiness estimating method of estimating, from a time-series signal of an eye-openness width of a subject, drowsiness of the subject, the drowsiness estimating method comprising:

filtering, by a filtering circuitry, the time-series signal of the eye-openness width so as to eliminate signal changes due to blinking of the subject therefrom to produce a filtered time-series signal of the eye-openness width;

calculating, by a feature calculator, a feature from at least the filtered time-series signal of the eye-openness width; and estimating, by a drowsiness estimator, a drowsiness evaluated value from the feature to produce an estimated result, wherein, in the feature detector, a first feature calculation circuit calculates at least a variation in the filtered time-series signal of the eye-openness width within a feature calculation window width ($T_M$) [sec] to produce the variation as a first feature.

(Supplementary Note 15)

The drowsiness estimating method according to Supplementary Note 14, wherein the time-series signal of the eye-openness width is a time-series signal of fs [frames/sec], wherein a relationship of $N=T_N \times fs$ holds, where N represents the number of frames and $T_N$ [sec] represents a filtering calculation window width, wherein the filtering circuitry filters the time-series signal of the eye-openness width per the filtering calculation window width ($T_N$) to substitute the time-series signal with a predetermined value and to produce a substituted signal as the filtered time-series signal of the eye-openness width.

(Supplementary Note 16)

The drowsiness estimating method according to Supplementary Note 15, wherein the filtering calculation window width ($T_N$) is not less than 0.1 [sec], wherein, in the filtering circuitry, a maximum value acquisition circuit acquires, as the predetermined value, a maximum value of the time-series signal of the eye-openness width within the filtering calculation window width ($T_N$).

(Supplementary Note 17)

The drowsiness estimating method according to Supplementary Note 15, wherein P is an integer which is not less than two and the filtering calculation window width ($T_N$) is not less than 0.2 [sec], wherein, in the filtering circuitry, a percentile calculation circuit calculates, as the predetermined value, a value of a (P−1)P-th percentile of the time-series signal of the eye-openness width within the filtering calculation window width ($T_N$) or an average value of the (P−1)P-th percentile and greater values.

(Supplementary Note 18)

The drowsiness estimating method according to Supplementary Note 15, wherein the filtering calculation window width ($T_N$) is not less than 1 [sec], wherein, in the filtering circuitry, an average value calculation circuit calculates, as the predetermined value, an average value of the time-series signal of the eye-openness width within the filtering calculation window width ($T_N$).

(Supplementary Note 19)

The drowsiness estimating method according to Supplementary Note 14, wherein the time-series signal of the eye-openness width is a time-series signal of fs [frames/sec], wherein, in the filtering circuitry, a low-pass filter having a cut-off frequency fc [Hz] which is sufficiently lower than the above-mentioned fs and is lower than 6 Hz, carries out low-pass filtering on the time-series signal of the eye-openness width to produce a low-pass filtered signal as the filtered time-series signal of the eye-openness width.

(Supplementary Note 20)

The drowsiness estimating method according to any one of Supplementary Notes 14 to 19, wherein, in the feature calculator, a second feature calculation circuit calculates inter-frame differences of the time-series signal of the eye-openness width, calculates a maximum value of the inter-frame differences within the feature calculation window width ($T_M$) [sec], and produces the maximum value as a second feature.

(Supplementary Note 21)

The drowsiness estimating method according to any one of Supplementary Notes 14 to 20, wherein, in the feature calculator, a third feature calculation circuit detects eye closure from the time-series signal of the eye-openness width, calculates an eye-closure ratio within the first predetermined time window width ($T_M$) [sec], and produces the eye-closure ratio as a third feature.

(Supplementary Note 22)

The drowsiness estimating method according to any one of Supplementary Notes 14 to 21, wherein, in the feature calculator, a fourth feature calculation circuit calculates motion differences of the eye-openness width between a left eye and a right eye from the time-series signal of the eye-openness width, calculates an average value of the motion differences within the feature calculation window width ($T_M$) [sec], and produces the average value of the motion differences as a fourth feature.

(Supplementary Note 23)

The drowsiness estimating method according to Supplementary Note 22, wherein, in the feature calculator, a fifth feature calculation circuit calculates differences between respective two adjacent values of the first through the fourth features, which are calculated by the first through the fourth feature calculation circuits in two adjacent feature calculation window widths ($T_M$) [sec], respectively, and produces a selected one of the differences as a fifth feature.

(Supplementary Note 24)

The drowsiness estimating method according to Supplementary Note 23, wherein, in the feature calculator, a sixth feature calculation circuit calculates logarithms of the first through the fifth features, which are calculated by the first through the fifth feature calculation circuits, respectively, and produces a selected one of the logarithms as a sixth feature.

(Supplementary Note 25)

The drowsiness estimating method according to Supplementary Note 24, wherein, in the feature calculator, a statistic calculation circuit calculates, within a statistic calculation window width ($T_K$) [sec] which is a multiple of the feature calculation window width ($T_M$) [sec], a statistic of a selected one of the first through the sixth features, which are calculated by the first through the sixth feature calculation circuits, respectively, per the feature calculation window width ($T_M$) [sec].

(Supplementary Note 26)

The drowsiness estimating method according to Supplementary Note 25, wherein the statistic calculation circuit calculates, as the statistic, at least one selected from an average value, a standard deviation, and a variance of a selected one of the first through the sixth features per the statistic calculation window width ($T_K$) [sec].

(Supplementary Note 27)

A drowsiness estimating program recording medium having recorded thereon a drowsiness estimating program for causing a computer to execute processing for estimating, from a time-series signal of an eye-openness width of a subject, drowsiness of the subject, the drowsiness estimating program causing the computer to execute:

a filtering procedure of filtering the time-series signal of the eye-openness width so as to eliminate signal changes due to blinking of the subject therefrom to produce a filtered time-series signal of the eye-openness width;

a feature calculation procedure of calculating a feature from at least the filtered time-series signal of the eye-openness width; and a drowsiness estimation procedure of estimating a drowsiness evaluated value from the feature to produce an estimated result, wherein the feature calculation procedure at least includes a first feature calculation procedure of calculating a variation in the filtered time-series signal of the eye-openness width within a feature calculation window width ($T_M$) [sec] to produce the variation as a first feature.

(Supplementary Note 28)

The drowsiness estimating program recording medium according to Supplementary Note 27, wherein the time-series signal of the eye-openness width is a time-series signal of fs [frames/sec], wherein a relationship of N=$T_N$×fs holds, where N represents the number of frames and $T_N$ [sec] represents a filtering calculation window width, wherein, in the filtering procedure, the computer is caused to filter the time-series signal of the eye-openness width per the filtering calculation window width ($T_N$) to substitute the time-series signal with a predetermined value, and to produce a substituted signal as the filtered time-series signal of the eye-openness width.

(Supplementary Note 29)

The drowsiness estimating program recording medium according to Supplementary Note 28, wherein the filtering calculation window width ($T_N$) is not less than 0.1 [sec], wherein the filtering procedure comprises a maximum value acquisition procedure of acquiring, as the predetermined value, a maximum value of the time-series signal of the eye-openness width within the filtering calculation window width ($T_N$).

(Supplementary Note 30)

The drowsiness estimating program recording medium according to Supplementary Note 28, wherein P is an integer which is not less than two and the filtering calculation window width ($T_N$) is not less than 0.2 [sec], wherein the filtering procedure comprises a percentile calculation procedure of calculating, as the predetermined value, a value of a (P−1)P-th percentile of the time-series signal of the eye-openness width within the filtering calculation window width ($T_N$) or an average value of the (P−1)P-th percentile and greater values.

(Supplementary Note 31)

The drowsiness estimating program recording medium according to Supplementary Note 28, wherein the filtering calculation window width ($T_N$) is not less than 1 [sec], wherein the filtering procedure comprises an average value calculation procedure of calculating, as the predetermined value, an average value of the time-series signal of the eye-openness width within the filtering calculation window width ($T_N$).

(Supplementary Note 32)

The drowsiness estimating program recording medium according to Supplementary Note 27, wherein the time-series signal of the eye-openness width is a time-series signal of fs [frames/sec], wherein the filtering procedure comprises a procedure of carrying out, using a low-pass filter having a cut-off frequency fc [Hz] which is sufficiently lower than the above-mentioned fs and is lower than 6 Hz, low-pass filtering on the time-series signal of the eye-openness width, and producing a low-pass filtered signal as the filtered time-series signal of the eye-openness width.

(Supplementary Note 33)

The drowsiness estimating program recording medium according to any one of Supplementary Notes 27 to 32, wherein the feature calculation procedure further comprises a second feature calculation procedure of calculating inter-frame differences of the time-series signal of the eye-openness width, calculating a maximum value of the inter-frame differences within the feature calculation window width ($T_M$) [sec], and producing the maximum value as a second feature.

(Supplementary Note 34)

The drowsiness estimating program recording medium according to any one of Supplementary Notes 27 to 33, wherein the feature calculation procedure further comprises a third feature calculation procedure of detecting eye closure from the time-series signal of the eye-openness width, calculating an eye-closure ratio within the first predetermined time window width ($T_M$) [sec], and producing the eye-closure ratio as a third feature.

(Supplementary Note 35)

The drowsiness estimating program recording medium according to any one of Supplementary Notes 27 to 34, wherein the feature calculation procedure further comprises a fourth feature calculation procedure of calculating motion differences of the eye-openness width between a left eye and a right eye from the time-series signal of the eye-openness width, calculating an average value of the motion differences within the feature calculation window width ($T_M$) [sec], and producing the average value of the motion differences as a fourth feature.

(Supplementary Note 36)

The drowsiness estimating program recording medium according to Supplementary Note 35, wherein the feature calculation procedure further comprises a fifth feature calculation procedure of calculating differences between respective two adjacent values of the first through the fourth features, which are calculated by the first through the fourth feature calculation procedures in two adjacent feature calculation window widths ($T_M$) [sec], respectively, and producing a selected one of the differences as a fifth feature.

(Supplementary Note 37)

The drowsiness estimating program recording medium according to Supplementary Note 36, wherein the feature calculation procedure further comprises a sixth feature calculation procedure of calculating logarithms of the first through the fifth features, which are calculated by the first through the fifth feature calculation procedures, respectively, and producing a selected one of the logarithms as a sixth feature.

(Supplementary Note 38)

The drowsiness estimating program recording medium according to Supplementary Note 37, wherein the feature calculation procedure further comprises a statistic calculation procedure of calculating, within a statistic calculation window width ($T_K$) [sec] which is a multiple of the feature calculation window width ($T_M$) [sec], a statistic of a selected one of the first through the sixth features, which are calculated by the first through the sixth feature calculation procedures, respectively, per the feature calculation window width ($T_M$) [sec].

(Supplementary Note 39)

The drowsiness estimating program recording medium according to Supplementary Note 38, wherein the statistic calculation procedure comprising calculating, as the statistic, at least one selected from an average value, a standard deviation, and a variance of a selected one of the first through the sixth features per the statistic calculation window width ($T_K$) [sec].

INDUSTRIAL APPLICABILITY

The drowsiness estimation device according to this invention is applicable to uses of estimating drowsiness of a staff member who works in an office or a driver who drives a car or the like.

REFERENCE SIGNS LIST

10 camera
20 subject
20L left eye
20R right eye
100~100H drowsiness estimating device
120 eye-openness width detector
122 left-eye eye-openness width detection circuit
124 right-eye eye-openness width detection circuit
126 average value calculation circuit
140~140D filtering circuitry
140-1 main filtering circuit
140-2 first auxiliary filtering circuit
140-2 second auxiliary filtering circuit
142 maximum value acquisition circuit
144 percentile calculation circuit
146 average value calculation circuit
148 low-pass filter
160~160H feature calculator
161 variation calculation circuit (first feature calculation circuit)
162 maximum difference value calculation circuit (second feature calculation circuit)
163 eye-closure ratio calculation circuit (third feature calculation circuit)
164 motion-difference average value calculation circuit (fourth feature calculation circuit)
165 adjacent-difference calculation circuit (fifth feature calculation circuit)
166 logarithm calculation circuit (sixth feature calculation circuit)
167 average value calculation circuit (seventh feature calculation circuit)
168 standard deviation calculation circuit (eighth feature calculation circuit)
169 variance calculation circuit (ninth calculation circuit)
180 drowsiness estimator

The invention claimed is:

1. A drowsiness estimating device for estimating, from a time-series signal of an eye-openness width of a subject, drowsiness of the subject, the drowsiness estimating device comprising:
   a filtering circuitry configured to filter the time-series signal of the eye-openness width so as to eliminate signal changes due to blinking having a time interval of 0.1 to 0.15 [sec] of the subject therefrom to produce a filtered time-series signal of the eye-openness width;
   a feature calculator configured to calculate a feature from at least the filtered time-series signal of the eye-openness width; and
   a drowsiness estimator configured to estimate a drowsiness evaluated value from the feature to produce an estimated result,
   wherein the feature calculator at least includes a first feature calculation circuit configured to calculate a variation in the filtered time-series signal of the eye-openness width within a feature calculation window width ($T_M$) [sec] to produce the variation as a first feature,
   wherein the time-series signal of the eye-openness width is a time-series signal of fs [frames/sec],
   wherein a relationship of $N=T_N \times fs$ holds, where N represents the number of frames and $T_N$ [sec] represents a filtering calculation window width,
   wherein the filtering circuitry is configured to filter the time-series signal of the eye-openness width per the filtering calculation window width ($T_N$) to produce the filtered time-series signal of the eye-openness width, and
   wherein the filtering calculation window width ($T_N$) [sec] is lain in a range between 0.1 [sec] and 1 [sec].

2. The drowsiness estimating device as claimed in claim 1,
   wherein the filtering circuitry is configured to filter the time-series signal of the eye-openness width per the filtering calculation window width ($T_N$) to substitute the time-series signal with a predetermined value, and to produce a substituted signal as the filtered time-series signal of the eye-openness width.

3. The drowsiness estimating device as claimed in claim 2,
   wherein the filtering calculation window width ($T_N$) is not less than 0.1 [sec],
   wherein the filtering circuitry comprises a maximum value acquisition circuit configured to acquire, as the predetermined value, a maximum value of the time-series signal of the eye-openness width within the filtering calculation window width ($T_N$).

4. The drowsiness estimating device as claimed in claim 2,
   wherein P is an integer which is not less than two and the filtering calculation window width ($T_N$) is not less than 0.2 [sec],
   wherein the filtering circuitry comprises a percentile calculation circuit configured to calculate, as the predetermined value, a value of a (P−1)P-th percentile of the time-series signal of the eye-openness width within the filtering calculation window width ($T_N$) or an average value of the (P−1)P-th percentile and greater values.

5. The drowsiness estimating device as claimed in claim 2,
   wherein the filtering calculation window width ($T_N$) is equal to 1 [sec],
   wherein the filtering circuitry comprises an average value calculation circuit configured to calculate, as the predetermined value, an average value of the time-series signal of the eye-openness width within the filtering calculation window width ($T_N$).

6. The drowsiness estimating device as claimed in claim 1,
   wherein the filtering circuitry comprises a low-pass filter having a cut-off frequency fc [Hz] which is sufficiently lower than the above-mentioned fs and is not higher than 6 Hz.

7. The drowsiness estimating device as claimed in claim 1,
   wherein the feature calculator further comprises a second feature calculation circuit configured to calculate inter-frame differences of the time-series signal of the eye-openness width, to calculate a maximum value of the inter-frame differences within the feature calculation window width ($T_M$) [sec], and to produce the maximum value as a second feature.

8. The drowsiness estimating device as claimed in claim 7,
   wherein the feature calculator further comprises a third feature calculation circuit configured to detect eye closure from the time-series signal of the eye-openness width, to calculate an eye-closure ratio within the feature calculation window width ($T_M$) [sec], and to produce the eye-closure ratio as a third feature.

9. The drowsiness estimating device as claimed in claim 8,
   wherein the feature calculator further comprises a fourth feature calculation circuit configured to calculate motion differences of the eye-openness width between a left eye and a right eye from the time-series signal of the eye-openness width, to calculate an average value of the motion differences within the feature calculation window width ($T_M$) [sec], and to produce the average value of the motion differences as a fourth feature.

10. The drowsiness estimating device as claimed in claim 9,
    wherein the feature calculator further comprises a fifth feature calculation circuit configured to calculate differences between respective two adjacent values of the first through the fourth features, which are calculated by the first through the fourth feature calculation circuits in two adjacent feature calculation window widths ($T_M$) [sec], respectively, and to produce a selected one of the differences as a fifth feature.

11. The drowsiness estimating device as claimed in claim 10,
    wherein the feature calculator further comprises a sixth feature calculation circuit configured to calculate logarithms of the first through the fifth features, which are calculated by the first through the fifth feature calculation circuits, respectively, and to produce a selected one of the logarithms as a sixth feature.

12. The drowsiness estimating device as claimed in claim 11,
    wherein the feature calculator further comprises a statistic calculation circuit configured to calculate, within a statistic calculation window width ($T_K$) [sec] which is a multiple of the feature calculation window width ($T_M$) [sec], a statistic of a selected one of the first through the sixth features, which are calculated by the first through the sixth feature calculation circuits, respectively, per the feature calculation window width ($T_M$) [sec].

13. The drowsiness estimating device as claimed in claim 12,
wherein the statistic calculation circuit is configured to calculates, as the statistic, at least one selected from an average value, a standard deviation, and a variance of a selected one of the first through the sixth features per the statistic calculation window width ($T_K$) [sec].

14. The drowsiness estimating device as claimed in claim 1,
wherein the feature calculator further comprises a third feature calculation circuit configured to detect eye closure from the time-series signal of the eye-openness width, to calculate an eye-closure ratio within the feature calculation window width ($T_M$) [sec], and to produce the eye-closure ratio as a third feature.

15. The drowsiness estimating device as claimed in claim 1,
wherein the feature calculator further comprises a fourth feature calculation circuit configured to calculate motion-differences of the eye-openness width between a left eye and a right eye from the time-series signal of the eye-openness width, to calculate an average value of the motion-differences within the feature calculation window width ($T_M$) [sec], and to produce the average value of the motion-differences as a fourth feature.

16. The drowsiness estimating device as claimed in claim 1,
wherein the feature calculator further comprises a fifth feature calculation circuit configured to calculate a difference between two adjacent values of the first feature in two adjacent feature calculation window widths ($T_M$) [sec] to produce the difference as a fifth feature.

17. The drowsiness estimating device as claimed in claim 1,
wherein the feature calculator further comprises a sixth feature calculation circuit configured to calculate a logarithm of the first feature to produce the logarithm as a sixth feature.

18. The drowsiness estimating device as claimed in claim 1,
wherein the feature calculator further comprises a statistic calculation circuit configured to calculate, within a statistic calculation window width ($T_K$) [sec] which is a multiple of the feature calculation window width ($T_M$) [sec], a statistic of the first feature per the feature calculation window width ($T_M$) [sec].

19. A drowsiness estimating method of estimating, from a time-series signal of an eye-openness width of a subject, drowsiness of the subject, the drowsiness estimating method comprising:
filtering the time-series signal of the eye-openness width so as to eliminate signal changes due to blinking having a time interval of 0.1 to 0.15 [sec] of the subject therefrom to produce a filtered time-series signal of the eye-openness width;
calculating a feature from at least the filtered time-series signal of the eye-openness width; and
estimating a drowsiness evaluated value from the feature to produce an estimated result,
wherein the calculating calculates at least a variation in the filtered time-series signal of the eye-openness width within a feature calculation window width ($T_M$) [sec] to produce the variation as a first feature,
wherein the time-series signal of the eye-openness width is a time-series signal of fs [frames/sec],
wherein a relationship of N=$T_N$×fs holds, where N represents the number of frames and $T_N$ [sec] represents a filtering calculation window width,
wherein the filtering is to filter the time-series signal of the eye-openness width per the filtering calculation window width ($T_N$) to produce the filtered time-series signal of the eye-openness width, and
wherein the filtering calculation window width ($T_N$) [sec] is lain in a range between 0.1 [sec] and 1 [sec].

20. A non-transitory drowsiness estimating program recording medium having recorded thereon a drowsiness estimating program for causing a computer to execute processing for estimating, from a time-series signal of an eye-openness width of a subject, drowsiness of the subject, the drowsiness estimating program causing the computer to execute:
a filtering procedure of filtering the time-series signal of the eye-openness width so as to eliminate signal changes due to blinking having a time interval of 0.1 to 0.15 [sec] of the subject therefrom to produce a filtered time-series signal of the eye-openness width;
a feature calculation procedure of calculating a feature from at least the filtered time-series signal of the eye-openness width; and
a drowsiness estimation procedure of estimating a drowsiness evaluated value from the feature to produce an estimated result,
wherein the feature calculation procedure at least includes a first feature calculation procedure of calculating a variation in the filtered time-series signal of the eye-openness width within a feature calculation window width ($T_M$) [sec] to produce the variation as a first feature,
wherein the time-series signal of the eye-openness width is a time-series signal of fs [frames/sec],
wherein a relationship of N=$T_N$×fs holds, where N represents the number of frames and $T_N$ [sec] represents a filtering calculation window width,
wherein the filtering procedure is of filtering the time-series signal of the eye-openness width per the filtering calculation window width ($T_N$) to produce the filtered time-series signal of the eye-openness width, and
wherein the filtering calculation window width ($T_N$) [sec] is lain in a range between 0.1 [sec] and 1 [sec].

* * * * *